US011684074B2

(12) United States Patent
Janow et al.

(10) Patent No.: US 11,684,074 B2
(45) Date of Patent: Jun. 27, 2023

(54) RICE PRODUCTS AND SYSTEMS AND METHODS FOR MAKING THEREOF

(71) Applicant: Axiom Foods, Inc., Los Angeles, CA (US)

(72) Inventors: David Janow, Los Angeles, CA (US); Robert E. Cadwalader, Los Angeles, CA (US)

(73) Assignee: Axiom Foods, Inc., Los Angeles, CA (US)

( * ) Notice: Subject to any disclaimer, the term of this patent is extended or adjusted under 35 U.S.C. 154(b) by 258 days.

(21) Appl. No.: 16/677,508

(22) Filed: Nov. 7, 2019

(65) Prior Publication Data

US 2020/0138054 A1 May 7, 2020

Related U.S. Application Data

(63) Continuation of application No. PCT/US2018/032138, filed on May 10, 2018.

(60) Provisional application No. 62/505,461, filed on May 12, 2017.

(51) Int. Cl.
| | | |
|---|---|---|
| A23J 1/12 | (2006.01) | |
| A23L 7/104 | (2016.01) | |
| A23L 29/30 | (2016.01) | |
| A23L 29/212 | (2016.01) | |
| A23J 3/34 | (2006.01) | |

(52) U.S. Cl.
CPC .............. *A23J 1/125* (2013.01); *A23J 3/34* (2013.01); *A23L 7/107* (2016.08); *A23L 29/212* (2016.08); *A23L 29/35* (2016.08)

(58) Field of Classification Search
CPC ... A23J 1/125; A23J 3/34; A23L 7/107; A23L 29/35; A23L 29/212
USPC ............................................................ 426/18
See application file for complete search history.

(56) References Cited

U.S. PATENT DOCUMENTS

| 4,377,601 A | 3/1983 | Dreese et al. |
| 4,830,861 A * | 5/1989 | Puski ............. C12Y 302/01001 426/18 |
| 4,876,096 A * | 10/1989 | Mitchell .......... C12Y 302/0102 426/28 |
| 4,990,344 A | 2/1991 | Euber et al. |
| 5,518,741 A | 5/1996 | Choudhary |
| 5,569,458 A | 10/1996 | Greenberg |
| 5,637,324 A | 6/1997 | Bland |

(Continued)

FOREIGN PATENT DOCUMENTS

| CN | 103555795 | 2/2014 |
| CN | 103621852 | 3/2014 |

(Continued)

OTHER PUBLICATIONS

Kuiken, K. A. et al. J. Biol. Chem. 171: 551-560 (Year: 1947).*

(Continued)

*Primary Examiner* — Hamid R Badr
(74) *Attorney, Agent, or Firm* — Knobbe, Martens, Olsen & Bear LLP

(57) ABSTRACT

Systems and methods for manufacturing maltodextrin and protein nutritional products from rice are disclosed. Some embodiments include: milling hydrated rice, digesting with an α-amylase enzyme to form a mixture of maltodextrin and protein, and separating the protein and maltodextrin from one another.

9 Claims, 7 Drawing Sheets

(56) References Cited

U.S. PATENT DOCUMENTS

| | | |
|---|---|---|
| 5,716,801 A | 2/1998 | Nielsen et al. |
| 5,753,296 A | 5/1998 | Girsh |
| 5,889,040 A | 3/1999 | Beale et al. |
| 6,221,418 B1 | 4/2001 | Bergenfield et al. |
| 6,242,033 B1 | 6/2001 | Sander |
| 6,245,377 B1 | 6/2001 | Tao |
| 6,602,517 B2 | 8/2003 | Darland et al. |
| 6,713,082 B2 | 3/2004 | Siemensma et al. |
| 6,774,111 B1 | 8/2004 | Wolf et al. |
| 6,875,456 B2 | 4/2005 | Delest et al. |
| 6,923,995 B2 | 8/2005 | Highman et al. |
| 6,929,793 B2 | 8/2005 | Spivey-Krobath et al. |
| 6,989,171 B2 | 1/2006 | Portman |
| 7,097,870 B2 | 8/2006 | Funk et al. |
| 7,147,882 B2 | 12/2006 | Girsh |
| 7,220,442 B2 | 5/2007 | Gautam et al. |
| 7,563,473 B2 | 7/2009 | Scanlin et al. |
| 7,579,024 B2 | 8/2009 | Morrissey |
| 7,678,406 B2 | 3/2010 | Heydtmann et al. |
| 7,691,424 B2 | 4/2010 | Axelrod |
| 7,740,893 B2 | 6/2010 | Portman |
| 7,744,930 B2 | 6/2010 | Fisher et al. |
| 7,754,256 B2 | 7/2010 | Dennison |
| 7,759,093 B2 | 7/2010 | Callen et al. |
| 7,790,176 B2 | 9/2010 | Morrissey |
| 7,790,670 B2 | 9/2010 | Ward et al. |
| 7,790,688 B2 | 9/2010 | Wolfe et al. |
| 7,794,770 B2 | 9/2010 | Sherwood et al. |
| 7,799,363 B2 | 9/2010 | Sherwood et al. |
| 7,879,382 B2 | 2/2011 | Tuason et al. |
| 7,906,160 B2 | 3/2011 | Sherwood et al. |
| 7,943,578 B2 | 5/2011 | Ogura et al. |
| 8,017,168 B2 | 9/2011 | Prakash et al. |
| 8,178,487 B2 | 5/2012 | Boza et al. |
| 8,192,769 B2 | 6/2012 | Wester et al. |
| 8,221,817 B2 | 7/2012 | Girsh |
| 8,278,068 B2 | 10/2012 | Vielhaber et al. |
| 8,299,034 B2 | 10/2012 | Offord Cavin et al. |
| 8,383,183 B2 | 2/2013 | Prakash et al. |
| 8,425,930 B2 | 4/2013 | Barboza et al. |
| 8,445,692 B2 | 5/2013 | Karanewsky et al. |
| 8,895,088 B2 | 11/2014 | Matsunaga et al. |
| 8,956,676 B2 | 2/2015 | Hansen et al. |
| 9,034,402 B2 | 5/2015 | Wong et al. |
| 9,820,504 B2 | 11/2017 | Janow et al. |
| 9,907,331 B2 | 3/2018 | Janow |
| 10,251,415 B2 | 4/2019 | Janow et al. |
| 2001/0007690 A1 | 7/2001 | Girsh |
| 2001/0031729 A1 | 10/2001 | Siemensma et al. |
| 2002/0051826 A1 | 5/2002 | Darland et al. |
| 2002/0197352 A1 | 12/2002 | Portman |
| 2003/0064135 A1 | 4/2003 | Portman |
| 2003/0165606 A1 | 9/2003 | Lasekan et al. |
| 2003/0190381 A1 | 10/2003 | Bland et al. |
| 2004/0005305 A1 | 1/2004 | Spivey-Krobath et al. |
| 2004/0013771 A1 | 1/2004 | Funk et al. |
| 2004/0022926 A1 | 2/2004 | Bartocci et al. |
| 2004/0033292 A1 | 2/2004 | Portman |
| 2004/0047896 A1 | 3/2004 | Malnoe et al. |
| 2004/0067279 A1 | 4/2004 | Delest et al. |
| 2004/0131744 A1 | 7/2004 | Kunst et al. |
| 2004/0166203 A1 | 8/2004 | Gautam et al. |
| 2004/0171690 A1 | 9/2004 | Ammann et al. |
| 2004/0197380 A1 | 10/2004 | Wolf et al. |
| 2004/0219188 A1 | 11/2004 | Comer et al. |
| 2004/0220118 A1 | 11/2004 | Bland et al. |
| 2004/0241664 A1 | 12/2004 | Dekker et al. |
| 2005/0002989 A1 | 1/2005 | Palmer et al. |
| 2005/0079232 A1 | 4/2005 | Offord-Cavin et al. |
| 2005/0100617 A1 | 5/2005 | Malnoe et al. |
| 2005/0106218 A1 | 5/2005 | Ward et al. |
| 2005/0152887 A1 | 7/2005 | Ernest |
| 2005/0153019 A1 | 7/2005 | Fuchs et al. |
| 2005/0181019 A1 | 8/2005 | Palmer et al. |
| 2005/0281792 A1 | 12/2005 | Short et al. |
| 2006/0019009 A1 | 1/2006 | Keller et al. |
| 2006/0034954 A1 | 2/2006 | Bland et al. |
| 2006/0088651 A1 | 4/2006 | Sandoval et al. |
| 2006/0121172 A1 | 6/2006 | Portman |
| 2006/0160189 A1 | 7/2006 | Hammond |
| 2006/0171993 A1 | 8/2006 | Barrett-Reis et al. |
| 2006/0182784 A1 | 8/2006 | Wester et al. |
| 2006/0193949 A1 | 8/2006 | Portman |
| 2006/0210697 A1 | 9/2006 | Mower |
| 2006/0239987 A1 | 10/2006 | Foster |
| 2006/0240169 A1 | 10/2006 | Heydtmann et al. |
| 2006/0246005 A1 | 11/2006 | Yang et al. |
| 2006/0257530 A1 | 11/2006 | Hoffpauer |
| 2006/0275506 A1 | 12/2006 | Fisher et al. |
| 2006/0286279 A1 | 12/2006 | Eastman et al. |
| 2007/0087097 A1 | 4/2007 | Cheng |
| 2007/0092629 A1 | 4/2007 | Scanlin et al. |
| 2007/0116840 A1 | 5/2007 | Prakash et al. |
| 2007/0128333 A1 | 6/2007 | Tuason et al. |
| 2007/0141018 A1 | 6/2007 | Courtois et al. |
| 2007/0148307 A1 | 6/2007 | Sherwood et al. |
| 2007/0154614 A1 | 7/2007 | Sherwood et al. |
| 2007/0207132 A1 | 9/2007 | Speelmans et al. |
| 2008/0009440 A1 | 1/2008 | Kodera et al. |
| 2008/0020098 A1 | 1/2008 | Gautam et al. |
| 2008/0050498 A1 | 2/2008 | Sherwood et al. |
| 2008/0089961 A1 | 4/2008 | Morrissey |
| 2008/0107775 A1 | 5/2008 | Prakash et al. |
| 2008/0145511 A1 | 6/2008 | Irwin et al. |
| 2008/0206430 A1 | 8/2008 | Avila |
| 2008/0233245 A1 | 9/2008 | White et al. |
| 2008/0268038 A1 | 10/2008 | Wolfe |
| 2008/0286433 A1 | 11/2008 | Simpson et al. |
| 2008/0292765 A1 | 11/2008 | Prakash et al. |
| 2008/0299145 A1 | 12/2008 | Morrissey |
| 2009/0011083 A1 | 1/2009 | Wong et al. |
| 2009/0018196 A1 | 1/2009 | Bjork et al. |
| 2009/0053378 A1 | 2/2009 | Prakash et al. |
| 2009/0060883 A1 | 3/2009 | Offord-Cavin et al. |
| 2009/0061068 A1 | 3/2009 | Marshman et al. |
| 2009/0075861 A1 | 3/2009 | Schwartz |
| 2009/0075862 A1 | 3/2009 | Boza et al. |
| 2009/0098261 A1 | 4/2009 | Park et al. |
| 2009/0105188 A1 | 4/2009 | Giannone et al. |
| 2009/0131331 A1 | 5/2009 | Edens et al. |
| 2009/0181903 A1 | 7/2009 | Wolfe et al. |
| 2009/0203592 A1 | 8/2009 | Beermann |
| 2009/0203606 A1 | 8/2009 | Wolfe et al. |
| 2009/0221502 A1 | 9/2009 | Yatcilla et al. |
| 2009/0238893 A1 | 9/2009 | Langford et al. |
| 2009/0269416 A1 | 10/2009 | Wedekind et al. |
| 2009/0275505 A1 | 11/2009 | Wedekind |
| 2009/0297689 A1 | 12/2009 | Edens et al. |
| 2009/0298113 A1 | 12/2009 | Vielhaber et al. |
| 2009/0298767 A1 | 12/2009 | Rowney et al. |
| 2009/0304823 A1 | 12/2009 | Offord Cavin et al. |
| 2009/0318368 A1 | 12/2009 | Ogura et al. |
| 2009/0325888 A1 | 12/2009 | Edens et al. |
| 2010/0028466 A1 | 2/2010 | Hitzfelo et al. |
| 2010/0068304 A1 | 3/2010 | Wedekind et al. |
| 2010/0068369 A1 | 3/2010 | Girsh |
| 2010/0093658 A1 | 4/2010 | Kihara et al. |
| 2010/0098802 A1 | 4/2010 | Navarro |
| 2010/0099640 A1 | 4/2010 | Geuns et al. |
| 2010/0111915 A1 | 5/2010 | Isolauri et al. |
| 2010/0112635 A1 | 5/2010 | Edens et al. |
| 2010/0113368 A1 | 5/2010 | Edens |
| 2010/0130401 A1 | 5/2010 | Wester et al. |
| 2010/0158984 A1 | 6/2010 | Qvyjt |
| 2010/0159079 A1 | 6/2010 | Qvyjt |
| 2010/0166859 A1 | 7/2010 | Edens et al. |
| 2010/0184963 A1 | 7/2010 | Scanlin et al. |
| 2010/0190708 A1 | 7/2010 | Tsuno et al. |
| 2010/0196583 A1 | 8/2010 | Kawase et al. |
| 2010/0227007 A1 | 9/2010 | Romero et al. |
| 2010/0254949 A1 | 10/2010 | Barboza et al. |
| 2010/0286023 A1 | 11/2010 | Wolfe et al. |
| 2010/0297323 A1 | 11/2010 | Brooks et al. |
| 2010/0303961 A1 | 12/2010 | Brooks et al. |

(56) References Cited

U.S. PATENT DOCUMENTS

| | | |
|---|---|---|
| 2010/0303990 A1 | 12/2010 | Brooks et al. |
| 2010/0303991 A1 | 12/2010 | Karwowski et al. |
| 2010/0316782 A1 | 12/2010 | Shi et al. |
| 2011/0002900 A1 | 1/2011 | Mingrone et al. |
| 2011/0014328 A1 | 1/2011 | Rizvi et al. |
| 2011/0028416 A1 | 2/2011 | Offord Cavin et al. |
| 2011/0052729 A1 | 3/2011 | Golini |
| 2011/0086803 A1 | 4/2011 | De Roos et al. |
| 2011/0151097 A1 | 6/2011 | Tuason et al. |
| 2011/0152180 A1 | 6/2011 | Hettiarachchy |
| 2011/0172142 A1 | 7/2011 | Smith et al. |
| 2011/0189349 A1 | 8/2011 | Immig et al. |
| 2011/0233469 A1 | 9/2011 | Petersen |
| 2011/0236535 A1 | 9/2011 | Meehan |
| 2011/0250313 A1 | 10/2011 | Hwang et al. |
| 2011/0256282 A1 | 10/2011 | Piechocki et al. |
| 2011/0257087 A1 | 10/2011 | Krul et al. |
| 2011/0269185 A1 | 11/2011 | David |
| 2011/0274741 A1 | 11/2011 | Horton |
| 2011/0280988 A1 | 11/2011 | Ivy |
| 2011/0301085 A1 | 12/2011 | Wester et al. |
| 2011/0305798 A1 | 12/2011 | Steen |
| 2011/0314725 A1 | 12/2011 | Petrie et al. |
| 2011/0318464 A1 | 12/2011 | Prakash et al. |
| 2012/0027897 A1 | 2/2012 | Innocenzi |
| 2012/0039951 A1 | 2/2012 | Watson et al. |
| 2012/0040052 A1 | 2/2012 | Carrigan et al. |
| 2012/0040929 A1 | 2/2012 | Courtois et al. |
| 2012/0046369 A1 | 2/2012 | Nahas et al. |
| 2012/0082760 A1 | 4/2012 | Rosedale |
| 2012/0088796 A1 | 4/2012 | Karanewsky et al. |
| 2012/0100257 A1 | 4/2012 | Lambach et al. |
| 2012/0121612 A1 | 5/2012 | Tuscano et al. |
| 2012/0122935 A1 | 5/2012 | Giannone et al. |
| 2012/0122984 A1 | 5/2012 | Hillman et al. |
| 2012/0128832 A1 | 5/2012 | Smith |
| 2012/0128851 A1 | 5/2012 | Brooks et al. |
| 2012/0141443 A1 | 6/2012 | Prioult et al. |
| 2012/0149782 A1 | 6/2012 | Hitzfeld et al. |
| 2012/0164306 A1 | 6/2012 | Girsh |
| 2012/0171165 A1 | 7/2012 | Buck et al. |
| 2012/0171166 A1 | 7/2012 | Chow et al. |
| 2012/0171177 A1 | 7/2012 | Biehl et al. |
| 2012/0171178 A1 | 7/2012 | Fleith et al. |
| 2012/0172319 A1 | 7/2012 | Chow et al. |
| 2012/0177752 A1 | 7/2012 | Baxter et al. |
| 2012/0178672 A1 | 7/2012 | Wolf et al. |
| 2012/0183506 A1 | 7/2012 | Nutten et al. |
| 2012/0189715 A1 | 7/2012 | Baxter et al. |
| 2012/0189716 A1 | 7/2012 | Baxter et al. |
| 2012/0189717 A1 | 7/2012 | Baxter et al. |
| 2012/0196352 A1 | 8/2012 | Kim et al. |
| 2012/0196829 A1 | 8/2012 | Baxter et al. |
| 2012/0207882 A1 | 8/2012 | Sonnenburg |
| 2012/0207904 A1 | 8/2012 | Twombly et al. |
| 2012/0244125 A1 | 9/2012 | Verdu de Bercik et al. |
| 2012/0251512 A1 | 10/2012 | Farmer et al. |
| 2012/0276057 A1 | 11/2012 | Steenhout et al. |
| 2012/0282232 A1 | 11/2012 | Tobin et al. |
| 2012/0283180 A1 | 11/2012 | Hofman et al. |
| 2012/0288588 A1 | 11/2012 | Barron |
| 2012/0309092 A1 | 12/2012 | Spangenberg et al. |
| 2012/0315697 A1 | 12/2012 | Pettit et al. |
| 2012/0322992 A1 | 12/2012 | Ochiai et al. |
| 2012/0329756 A1 | 12/2012 | Courtois et al. |
| 2013/0011498 A1 | 1/2013 | Baxter et al. |
| 2013/0023468 A1 | 1/2013 | Hofman et al. |
| 2013/0052234 A1 | 2/2013 | Goldberg et al. |
| 2013/0065822 A1 | 3/2013 | Miller et al. |
| 2013/0090391 A1 | 4/2013 | Tan et al. |
| 2013/0101697 A1 | 4/2013 | Shimada et al. |
| 2013/0115329 A1 | 5/2013 | Savant et al. |
| 2013/0115330 A1 | 5/2013 | Savant et al. |
| 2013/0122139 A1 | 5/2013 | Savant et al. |
| 2013/0122148 A1 | 5/2013 | Savant et al. |
| 2013/0122180 A1 | 5/2013 | Brooks et al. |
| 2013/0129838 A1 | 5/2013 | Miller et al. |
| 2013/0129868 A1 | 5/2013 | Gulseren et al. |
| 2013/0130972 A1 | 5/2013 | Le Coutre et al. |
| 2013/0142903 A1 | 6/2013 | Duan et al. |
| 2013/0160165 A1 | 6/2013 | Reuzeau et al. |
| 2013/0171318 A1 | 7/2013 | Bovetto et al. |
| 2013/0195803 A1 | 8/2013 | German et al. |
| 2013/0202764 A1 | 8/2013 | Prakash et al. |
| 2013/0203645 A1 | 8/2013 | Moore et al. |
| 2013/0203663 A1 | 8/2013 | Mager et al. |
| 2013/0209373 A1 | 8/2013 | Mager et al. |
| 2013/0209587 A1 | 8/2013 | Mager et al. |
| 2014/0057999 A1* | 2/2014 | Beck .................... A23K 20/179 514/773 |
| 2015/0208688 A1 | 7/2015 | Mackay |
| 2015/0257411 A1 | 9/2015 | Janse et al. |
| 2018/0206544 A1 | 7/2018 | Janow et al. |
| 2019/0174803 A1 | 6/2019 | Cadwalader |
| 2019/0239548 A1 | 8/2019 | Janow et al. |
| 2020/0315234 A1 | 10/2020 | Janow et al. |
| 2020/0367537 A1 | 11/2020 | Cadwalader |
| 2021/0186077 A1 | 6/2021 | Janow et al. |
| 2021/0204572 A1 | 7/2021 | Cadwalader |

FOREIGN PATENT DOCUMENTS

| | | |
|---|---|---|
| CN | 104664182 | 6/2015 |
| CN | 105558763 | 5/2016 |
| CN | 105410598 | 4/2019 |
| EP | 0 369 818 | 5/1990 |
| EP | 1 112 693 | 7/2001 |
| EP | 1 738 659 | 1/2007 |
| JP | 2001-086954 | 4/2001 |
| JP | 2003-180275 | 7/2003 |
| JP | 2007-222053 | 9/2007 |
| JP | 2011-211929 | 10/2011 |
| WO | WO 95/003708 | 2/1995 |
| WO | WO 96/019120 | 6/1996 |
| WO | WO 96/034535 | 11/1996 |
| WO | WO 00/057711 | 10/2000 |
| WO | WO 01/021012 | 3/2001 |
| WO | WO 2004/047549 | 6/2004 |
| WO | WO 2006/047352 | 5/2006 |
| WO | WO 2007/035595 | 3/2007 |
| WO | WO 2008/144259 | 11/2008 |
| WO | WO 2010/071541 | 6/2010 |
| WO | WO 2011/089525 | 7/2011 |
| WO | WO 2011/149713 | 12/2011 |
| WO | WO 2012/021163 | 2/2012 |
| WO | WO 2012/024611 | 2/2012 |
| WO | WO 2012/027226 | 3/2012 |
| WO | WO 2012/051591 | 4/2012 |
| WO | WO 2012/106179 | 8/2012 |
| WO | WO 2012/130627 | 10/2012 |
| WO | WO 2012/135499 | 10/2012 |
| WO | WO 2012/141795 | 10/2012 |
| WO | WO 2012/170021 | 12/2012 |
| WO | WO 2013/036149 | 3/2013 |
| WO | WO 2013/092851 | 6/2013 |
| WO | WO 2014/036019 | 3/2014 |
| WO | WO 2014/138304 | 9/2014 |
| WO | WO 2016/172418 | 10/2016 |
| WO | WO 2018/026734 | 2/2018 |
| WO | WO 2018/035245 | 2/2018 |
| WO | WO 2018/209131 | 11/2018 |
| WO | WO 2019/161079 | 8/2019 |
| WO | WO 2019/241152 | 12/2019 |

OTHER PUBLICATIONS

Shih, F. F. et al. J. Am. Oil Chem. Soc. 01 (Abstract) (Year: 2000).*
"Activated Carbon", Wikipedia.org, Apr. 28, 2017, pp. 14, https://en.wikipedia.org/w/index.php?title=Activated_carbon&oldid=777695475.
Amazon.com, "Growing Naturals Rice Protein Chocolate Powder, 16.4 Ounce by Growing Naturals", Growing Naturals, https://www.amazon.com/Growing-Naturals-Protein-Chocolate-Ounces/dp/

(56) References Cited

OTHER PUBLICATIONS

B008U7ML70, confirmable publicly known date is Dec. 7, 2012, printed Dec. 13, 2017 in 5 pages.

Amazon.com, "Growing Naturals Rice Protein Isolate Powder, Vanilla Blast, 16.4 Ounce", Growing Naturals, http://www.amazon.com/Growing-Naturals-Protein-Isolate-Vanilla/dp/B005K0MFSA [See description of product], as printed Jun. 9, 2016 in 6 pages.

Axiom Foods, "Oryzatein® 80: Original, Silk, Ultra-Amino Acid Profile", Sep. 29, 2015, 1 page.

Barber, S., "Studies on the Chemistry and Technology of Foods, Valencia [Spain]," Revista de Agroquimica y Tecnologia de Alimentos, 1981, vol. 21, No. 2, pp. 175-184.

Burden, Ph.D., David W., "Guide to the Disruption of Biological Samples—2012", Version 1.1, Random Primers, Jan. 2012, No. 12, pp. 1-25.

Campbell et al., "International Society of Sports Nutrition Position Stand: Protein and Exercise", Journal of the International Society of Sports Nutrition, Sep. 26, 2007, vol. 4, No. 8, pp. 7.

Chen et al., "Preparation and Development of Rice Bran Beverage," Shipin Keji, Jingchu University of Technology, 2012, vol. 37 No. 9, p. 156-159, 165.

Chen et al., "Production of High-Fructose Rice Syrup and High-Protein Rice Flour from Broken Rice", Journal of the Science of Food and Agriculture, 1984, vol. 35, pp. 1128-1135.

Dapra et al., "Rice Protein-Concentrate Meal as a Potential Dietary Ingredient in Practical Diets for Blackspot Seabream *Pagellus bograraveo*: a Histological and Enzymatic Investigation," Journal of Fish Biology, Mar. 2009, vol. 74, No. 4, pp. 773-789.

Elissa, "Vegetarian Proteins: Rice Protein Review", Jan. 12, 2013 http://www.ultimatefatburner.com/bodybuilding/rice-protein.html, 3 pages.

Fujita et al., "Effect of Quality and Quantity of Dietary Protein on Free Amino Acids in Plasma and Tissues of Adult Rats," Journal of Nutritional Science and Vitaminology, 1981, vol. 27 No. 2, pp. 129-147.

Gaspari, Rich, "Clinical Muscle Presents Brown Rice Protein Concentrate by Rich Gaspari", http://www.youtube.com/watch?v=hDRtSyTNEhs single screen shot in 1 page, YouTube Video indicates an upload of Jan. 20, 2012.

Hamada, U.S., "Characterization and Functional Properties of Rice Bran Proteins Modified by Commercial Exoproteases and Endoproteases", Journal of Food Science, vol. 65, No. 2, 2000, pp. 305-310.

Hobbs, Larry, "Sweeteners from Starch: Production, Properties and Uses", Starch: Chemistry and Technology, Third Edition, Ch. 21, 2009, pp. 797-832.

Hou et al., "Protein Hydrolysates in Animal Nutrition: Industrial Production, Bioactive Peptides, and Functional Significance", Journal Animal Science Biotechnology, 2017, vol. 8, No. 24, pp. 23.

Hou et al., "Rice Protein Concentrate Partially Replaces Dried Whey in the Diet for Early-Weaned Piglets and Improves their Growth Performance," Journal of the Science of Food and Agriculture, 2008, vol. 88 No. 7, pp. 1187-1193.

Houston, et al., "Amino Acid Composition of Rice and Rice By-Products," Cereal Chemistry, Sep. 1969, vol. 46, No. 5, pp. 527-537.

Huang et al., "Effects of Rice-Duck Ecological Management Technique on Growth Performance and Meat Quality of Ducks," Hunan Nongye Daxue Xuebao, 2007, vol. 33 No. 6, pp. 714-717.

International Preliminary Report on Patentability received in PCT Application No. PCT/US2018/032138, dated Nov. 21, 2019 in 12 pages.

International Search Report and Written Opinion received in PCT Application No. PCT/US2018/032138, dated Aug. 8, 2018 in 15 pages.

Ishii et al., "A Rice Diet is Associated with Less Fat Synthesis/Accumulation than a Bread Diet before Exercise Therapy," Journal of Nutritional Science and Vitaminology, 2005, vol. 51 No. 5, pp. 349-354.

Jäger et al., "Comparison of Rice and Whey Protein Osolate Digestion Rate and Amino Acid Absorption", Journal of the International Society of Sports Nutrition, 2013, vol. 10, Suppl. 1, pp. 3.

Joy et al., "The Effects of 8 Weeks of Whey or Rice Protein supplementation on body composition and Exercise Performance," Nutrition Journal, 2013, vol. 12, No. 86, pp. 7.

Kalman et al., "Amino Acid Composition of an Organic Brown Rice Protein Concentrate and Isolate Compated to Soy and Whey Concentrates and Isolates", Foods, 2014, vol. 3, pp. 394-402.

Katz et al., "Rice Nightmare: Kwashiorkor in 2 Philadelphia-Area Infants Fed Rice Dream Beverage," Journal of the American Academy of Dermatology, May 2005, vol. 52, No. 5, pp. S69-S72.

Kikuchi, Mitsori, "The Functionality of Rice Protein and Rice Peptide," Food Style 21, 2009, vol. 13 No. 11, pp. 69-71.

Knott, Michelle, "Mainstream Muscle," FoodManufacture.co.uk, Oct. 31, 2012, http://web.archive.org/web/20130217113656/http://www.foodmanufacture.co.uk/Ingredients/Mainstream-muscle, pp. 2.

Koo et al., "Rice Protein-Based Infant Formula: Current Status and Future Development", Minerva Pediatrics, 2007, vol. 59, No. 1, pp. 35-41.

Li et al., "Effects of Rice Dreg Protein and its Hydrolysate on Growth Performance and Small Intestine Morphology of Early-Weaned Rats", Journal of the Science of Food and Agriculture, Mar. 2011, vol. 91, No. 4, pp. 687-693.

Liu et al., "Advances on Biosynthesis of Rice Seed Storage Proteins in Molecular Biology," Molecular Plant Breeding, 2008, vol. 6, No. 1, pp. 1-15.

"Maltodextrin", Wikipedia.org, Apr. 25, 2017, pp. 3, https://en.wikipedia.org/w/index.php?title=Maltodextrin&oldid=777180214.

Milo Ohr, Linda, "Nutraceuticals & Functional Foods," Food Technology, Jun. 2005, vol. 59, No. 6, pp. 84-100.

Mizukami et al., "Effect of Vegetable Protein Fed to Pregnant Rats on the Growth of the Young and Their Improved Nutritional Effect," Nippon Kasei Gakkaishi, 1992, vol. 43, No. 7, pp. 617-627.

Morita et al., "Mass Production Method for Rice Protein Isolate and Nutritional Evaluation", Journal of Food Science, 1993, vol. 58 No. 6, pp. 1393-1396.

Noel et al., "A Traditional Rice and Beans Pattern Is Associated with Metabolic Syndrome in Puerto Rican Older Adults," The Journal of Nutrition, 2009, vol. 139, No. 7, pp. 1360-1367.

Omstedt et al., "Effect of the Nutritional Value of Dietary Proteins on the Synthesis of Proteins in Skeletal Muscle," Näringsforskning, 1972, vol. 16, No. 4, pp. 193-202. [English Summary Only Available].

Omstedt et al., "The Influence of the Nutritive Value of Proteins on the Level of Protein Synthesis in Vitro in Rat Skeletal Muscle", British Journal of Nutrition, 1972, vol. 27, pp. 467-474.

Oujifard et al., "Fish Meal Replacement with Rice Protein Concentrate in a Practical Diet for the Pacific White Shrimp *Litopenaeus vannamei* Boone, 1931," Aquaculture International, Feb. 2012, vol. 20, No. 1, pp. 117-129.

Palmegiano et al., "Rice Protein Concentrate Meal as Potential Dietary Ingredient in Practical Diets for Blackspot Seabream (*Pagellus bograveo*)," Journal of Animal Physiology and Animal Nutrition, 2007, vol. 91 No. 5-6, pp. 235-239.

Palmegiano et al., "Rice Protein Concentrate Meal as Potential Dietary Ingredient in Practical Diets for Rainbow Trout (*Oncorhynchus mykiss*)," Aquaculture, 2006, vol. 258, p. 357-367.

"Pancreatin", Glowm.com, Mar. 9, 2011, pp. 2, https://web.archive.org/web/20110309024721/http://www.glowm.com/resources/glowm/cd/pages/drugs/p003.html.

Roohinejad et al. "Effect of Pre-Germination Time on Amino Acid Profile and Gamma Amino Butyric Acid (GABA) Contents in Different Varieties of Malaysian Brown Rice," International Journal of Food Properties, 2011, vol. 14, No. 6, pp. 1386-1399.

Santana et al., "Naturally Occurring Ingredients as Potential Antiaging Cosmetics," Latin American Journal of Pharmacy, 2011, vol. 30, No. 8, pp. 1531-1535.

Santos, et al., "Storage Protein Profile and Amino Acid Content in Wild Rice *Oryza glumaepatula*," Pesquisa Agropecuária Brasileira, Brasilia, Jan. 2013, vol. 48, No. 1, pp. 66-72.

(56) References Cited

OTHER PUBLICATIONS

Sharma et al., "Studies on Rice Bran and its Benefits—A Review", International Journal of Engineering Research and Applications, May 2015, vol. 5, No. 5, (Part 2), pp. 107-112.

Silyao et al., "Development of a Pilot System for Converting Sweet Potato Starch into Glucose Syrup", Habitation (Elmsford), 2003, vol. 9, No. 1-2, pp. 9-15. [Abstract Only].

Suh, Succ Jo, "Effects of Rice Dieton Rats," K'at'ollik Taehak Uihakpu Nonmunjip, 1963, vol. 7, pp. 1-31.

Takashi et al., "Rice Protein and Peptide for Sports Nutrition", Food Style Apr. 21, 2012, vol. 16, No. 4, pp. 66-68.

Tanphaichitr et al., "Dietary Lysine and Carnitine: Relation to Growth and Fatty Livers in Rats," Journal of Nutrition, 1976, vol. 106, No. 1, pp. 111-117.

Tome, Daniel, "Criteria and Markers for Protein Quality Assessment—A Review," British Journal of Nutrition, 2012, vol. 108, pp. S222-S229.

Torres-Fuentes et al., "Iron-Chelating Activity of Chickpea Protein Hydrolysate Peptides", Food Chemistry, 2012, vol. 134, pp. 1585-1588.

Vijayaraghavan, P. K., "The Hemopoietic Activity of Some Food Proteins," Indian Journal of Medical Research, 1955, vol. 43, No. 4, pp. 569-574.

Wang et al., "Beverage Based on Rice and Soybean Water-Soluble Extract," Ciencia e Tecnologia de Alimentos, 1997, vol. 17, No. 2, pp. 73-77.

Wang et al., "Preparation and Functional Properties of Rice Bran Protein Isolate", Journal of Agricultural Food Chemistry, vol. 47, 1999, pp. 411-416.

Weiner et al., "Rice Protein Increases Lean Body Mass, Muscle Hypertrophy, Power And Strength Comparable To Whey Protein Following Resistance Exercise," Poster presented at NSCA National Conference, Las Vegas, Jul. 10-13, 2013, pp. 3.

Yengkokpam et al., "Gelatinized Carbohydrates in the Diet of *Catla catla* Fingerlings: Effect of Levels and Sources on Nutrient Utilization, Body Composition and Tissue Enzyme Activities," Asian-Australasian Journal of Animal Sciences, Jan. 2007, vol. 20, No. 1, pp. 89-99.

Yin, Li-Jung, "Effect of Rice Koji Fermentation on the Characteristics of Mackerel Muscle," Journal of The Fisheries Society of Taiwan, 2005, vol. 32, No. 4, pp. 341-354.

Zazula, Magdalena, "Changes in Body Protein Level in Tree Sparrow (*Passer montanus* (L.)) Induced by High and Low Protein Diets," Ekologia Polska, 1984, vol. 32, No. 4, pp. 709-720.

Zhao et al., "Enhancing the Oxidative Stability of Food Emulsions with Rice Dreg Protein Hydrolysate", Food Research International, vol. 48, No. 2, 2012, pp. 876-884.

Celus et al., "Enzymatic Hydrolysis of Brewers' Spent Grain Proteins and Technofunctional Properties of the Resulting Hydrolysates", Journal of Agricultural and Food Chemistry, 2007, vol. 55, No. 21, pp. 8703-8710.

Treimo et al., "Enzymatic Solubilization of Proteins in Brewer's Spent Grain", Journal of Agricultural and Food Chemistry, 2008, vol. 56, No. 13, pp. 5359-5365.

\* cited by examiner

| ANALYTICAL RESULTS | | | | |
|---|---|---|---|---|
| SOLIDS | GLUCOSE | MALTOSE | TOTAL SUGARS | CALC DE |
| SYSTEMS AND METHODS FOR MAKING RICE PRODUCTS | SYSTEMS AND METHODS FOR MAKING RICE PRODUCTS | SYSTEMS AND METHODS FOR MAKING RICE PRODUCTS | SYSTEMS AND METHODS FOR MAKING RICE PRODUCTS | SYSTEMS AND METHODS FOR MAKING RICE PRODUCTS |
| 34 | 10.5 | 8.99 | 19.5 | 44.6 |
| 34.3 | 15.1 | 9.95 | 25.1 | 59.1 |
| 34.5 | 17 | 9.25 | 26.3 | 63.2 |
| 34.5 | 19 | 7.8 | 26.9 | 66.8 |
| 34.8 | 21.1 | 6.62 | 27.7 | 70.5 |
| 34.7 | 22.7 | 5.51 | 28.2 | 73.7 |
| 34.8 | 24.6 | 4.35 | 29 | 77.2 |
| 35.1 | 29.7 | 1.39 | 31.1 | 86.7 |
| 35.4 | 32.4 | 0.475 | 32.9 | 92.2 |
| 32.9 | 2.39 | 5.66 | 8.05 | 16.2 |
| 34.3 | 12.8 | 9.97 | 22.8 | 52.4 |
| 34.3 | 12.4 | 10.1 | 22.5 | 51.5 |
| 34 | 14 | 10.5 | 24.5 | 57.2 |
| 34.2 | 15.5 | 10.3 | 25.8 | 61.0 |
| 34.7 | 16.7 | 9.75 | 26.5 | 62.7 |
| 34.7 | 17.8 | 9.16 | 27 | 65.0 |
| 34.7 | 19.1 | 8.35 | 27.5 | 67.6 |
| 34.9 | 22.9 | 5.57 | 28.5 | 73.9 |
| 35.2 | 28.7 | 1.99 | 30.7 | 84.5 |
| 32.9 | 2.39 | 5.66 | 8.05 | 16.2 |
| 34.3 | 14 | 10.1 | 24.1 | 56.1 |
| 34.3 | 16.9 | 9.24 | 26.1 | 63.3 |
| 34.3 | 19.9 | 7.97 | 27.9 | 70.1 |
| 32.9 | 2.39 | 5.66 | 8.05 | 16.2 |
| 34 | 12.2 | 9.62 | 21.8 | 50.6 |
| 34 | 14.4 | 10.5 | 24.9 | 58.4 |
| 34.7 | 21.8 | 6.21 | 28 | 72.1 |
| 32.9 | 2.39 | 5.66 | 8.05 | 16.2 |
| 33.7 | 15.6 | 9.74 | 25.3 | 61.3 |
| 34 | 21.2 | 6.29 | 27.5 | 72.0 |
| 34.6 | 27 | 3.1 | 30.1 | 82.7 |
| 32.9 | 2.39 | 5.66 | 8.05 | 16.2 |
| 34.4 | 13.4 | 10.3 | 23.7 | 54.5 |
| 34.4 | 14.9 | 10.4 | 25.3 | 59.0 |

Fig. 1A

| ANALYTICAL RESULTS | | | | |
|---|---|---|---|---|
| SOLIDS | GLUCOSE | MALTOSE | TOTAL SUGARS | CALC DE |
| 34.4 | 16.4 | 9.93 | 26.3 | 62.7 |
| 34.7 | 19 | 8.24 | 27.2 | 67.1 |
| 32.9 | 2.39 | 5.66 | 8.05 | 16.2 |
| 33.9 | 8.57 | 7.59 | 16.2 | 36.9 |
| 33.8 | 10.3 | 8.92 | 19.2 | 44.2 |
| 34.1 | 11.7 | 9.76 | 21.5 | 49.2 |
| 34.2 | 14.7 | 10.3 | 25 | 58.6 |
| 32.9 | 2.39 | 5.66 | 8.05 | 16.2 |
| 34.3 | 17.3 | 9.07 | 26.4 | 64.2 |
| 34.5 | 19.7 | 7.29 | 27 | 68.1 |
| 34.4 | 22.4 | 5.81 | 28.2 | 73.9 |
| 34.6 | 27.3 | 2.19 | 29.5 | 82.2 |
| 32.9 | 2.39 | 5.66 | 8.05 | 16.2 |
| 19.9 | 8.23 | 4.89 | 13.1 | 54.1 |
| 17.2 | 9.88 | 4.14 | 14 | 70.0 |
| 17.2 | 11.3 | 3.5 | 14.8 | 76.3 |
| 17.3 | 13.3 | 1.81 | 15.1 | 82.3 |
| 32.9 | 2.39 | 5.66 | 8.05 | 16.2 |
| 25.7 | 10.6 | 7.98 | 18.6 | 57.4 |
| 26.1 | 12.4 | 7.65 | 20.1 | 62.8 |
| 25.9 | 13.6 | 6.82 | 20.4 | 66.2 |
| 26.1 | 17.3 | 4.66 | 22 | 75.6 |

Fig. 1B

| Amino Acid | AA g / 100 g Isolate | AA g / 100 g Protein |
|---|---|---|
| Alanine | 4.89 | 5.9 |
| Arginine | 6.63 | 8.01 |
| Aspartic Acid | 7.42 | 8.96 |
| Cysteine | 1.53 | 1.84 |
| Glutamic Acid | 14.76 | 17.83 |
| Glycine | 3.70 | 4.47 |
| Histidine* | 1.89 | 2.28 |
| Isoleucine*^ | 3.74 | 4.51 |
| Leucine*^ | 6.89 | 8.32 |
| Lysine* | 2.82 | 3.41 |
| Methionine* | 2.38 | 2.87 |
| Phenylalanine* | 4.42 | 5.34 |
| Proline | 3.97 | 4.80 |
| Serine | 4.06 | 4.91 |
| Threonine* | 3.03 | 3.66 |
| Tryptophan* | 1.25 | 1.51 |
| Tyrosine | 4.15 | 5.01 |
| Valine*^ | 5.24 | 6.33 |

*Essential Amino Acid

^Branched Chain Amino Acid

Fig. 6

RICE PRODUCTS AND SYSTEMS AND METHODS FOR MAKING THEREOF

CROSS-REFERENCE TO RELATED APPLICATIONS

This patent application is a continuation of International PCT Application No. PCT/US2018/032138, filed May 10, 2018, which claims the benefit of priority to U.S. Provisional Patent Application No. 62/505,461, filed May 12, 2017. The foregoing applications are fully incorporated herein by reference for all purposes.

BACKGROUND

Field

Disclosed herein are methods of making rice-based nutritional products from rice starch and rice protein.

Description of the Related Art

Cereal grains (such as rice and oats) have an important role providing nutrition to the population. Relative to other food sources (e.g., beef, poultry, and fish), grains provide a more sustainable food source for the expanding population.

SUMMARY

Some embodiments disclosed herein pertain to a method of manufacturing maltodextrin and protein from rice. In some embodiments, rice is milled. In some embodiments, the rice is treated with water to prepare a hydrated rice. In some embodiments, the hydrated rice is milled to form a milled rice slurry. In some embodiments, the slurry is agitated with a starch enzyme. In some embodiments, the slurry is agitated with an α-amylase enzyme until a mixture of dissolved maltodextrin and suspended protein is formed. In some embodiments the milled rice slurry is heated with a steam injected jet cooker to enhance the rate of conversion of starch to maltodextrin. In some embodiments, the maltodextrin and suspended protein is homogenized to form a homogenous mixture. In some embodiments, the protein and maltodextrin are separated into an isolated protein fraction and an isolated maltodextrin fraction. In some embodiments, the isolated protein fraction is treated with a hydrolyzing agent to provide a hydrolyzed protein.

In some embodiments, the protein and maltodextrin are separated from one another using one or more of decanters, microfiltration membrane systems, filter presses, vibrating screen filter, incline screen filter, or combinations thereof.

In some embodiments, the hydrolyzing agent is a base. In some embodiments, the hydrolyzing agent is a protease enzyme. In some embodiments, the protease enzyme is an exoprotease or an endoprotease.

In some embodiments, the hydrolyzed protein is homogenized using a two-stage homogenizer.

In some embodiments, the hydrolyzed protein is dried using by a process selected from spraying into a dryer, drying in a drum dryer, or drying in a paddle dryer, evaporating at reduced temperature and/or under low pressure (e.g., less than or equal to about: 0.95 atm, 0.9 atm, 0.7 atm, 0.5 atm, 0.3 atm, 0.1 atm, or ranges including and/or spanning the aforementioned values), by heating, or combinations thereof. In some embodiments, the hydrolyzed protein is dried to provide a powder.

In some embodiments, upon mixing about 20 g of the protein powder in 12 fluid ounces of water, the protein product remains in suspension without visible and/or measurable sedimentation for a period of at least about a week.

In some embodiments, the isolated maltodextrin fraction is treated with glucoamylase to provide a rice syrup. In some embodiments, the rice syrup has a dextrose equivalent ranging from about 43 to about 65. In some embodiments, the rice syrup is processed through an activated carbon column, and/or ultrafilter, and/or nanofilter to decolor and deproteinate, and/or process through a de-ionizing column.

Some embodiments pertain to a method of manufacturing maltodextrin and protein from rice comprising treating rice with water to prepare a hydrated rice. In some embodiments, the hydrated rice is milled to form a milled rice slurry. In some embodiments, the slurry is agitated with an α-amylase enzyme until a mixture of dissolved maltodextrin and suspended protein is formed. In some embodiments the milled rice slurry is heated with a steam injected jet cooker to enhance the rate of conversion of starch to maltodextrin. In some embodiments, the maltodextrin and suspended protein is homogenized to form a homogenous mixture. In some embodiments, the protein and maltodextrin is separated using a microfiltration membrane into an isolated protein fraction and an isolated maltodextrin fraction.

In some embodiments, the isolated protein fraction is treated with a hydrolyzing agent to provide a hydrolyzed protein. In some embodiments, the hydrolyzing agent is a base. In some embodiments, the hydrolyzing agent is a protease enzyme. In some embodiments, the enzyme is an exoprotease or an endoprotease.

In some embodiments, the hydrolyzed protein is homogenized using a two-stage homogenizer. In some embodiments, the hydrolyzed protein is dried to provide a powder.

In some embodiments, upon mixing about 20 g of the protein powder in 12 fluid ounces of water, the protein product remains in suspension without visible and/or measurable sedimentation for a period of at least about a week.

In some embodiments, the isolated maltodextrin fraction is treated with glucoamylase to provide a rice syrup. In some embodiments, the rice syrup has a dextrose equivalent ranging from about 43 to about 65. In some embodiments, the rice syrup is treated by passing it through an activated carbon column, and/or ultrafilter, and/or nanofilter to decolor and deproteinate, and/or process through a de-ionizing column.

Some embodiments pertain to a protein powder comprising a hydrolyzed rice protein. In some embodiments, upon mixing about 20 g of the protein powder in 12 fluid ounces of water, the protein remains in suspension without sedimentation for a period of at least about a week.

Some embodiments pertain to a syrup comprising an enzyme-hydrolyzed maltodextrin having a dextrose equivalent ranging from about 43 to about 98.

Some embodiments pertain to a protein powder made using a method of any one of the preceding or following methods or steps. Some embodiments pertain to a rice syrup made using a method of any one of the preceding or following methods or steps.

In some embodiments, the method comprises isolating maltodextrin and/or protein from grain rice. In some embodiments, the method includes a step of receiving paddy rice. In some embodiments, husks are removed from the rice to prepare de-husked brown rice. In some embodiments, the rice is de-husked by subjecting the rice to a husk breaker. In some embodiments, brown rice can be used as an alternative or in addition to paddy rice. In some embodiments, bran is removed from the de-husked/brown rice. In some embodiments, the de-husked/brown rice with removed bran is passed through a whitener machine and is whitened to provide a white rice feedstock. In some embodiments, the whitened rice is treated with water to prepare wet rice and/or hydrated rice. In some embodiments, white rice/white rice brokens are used as an alternative to paddy rice and brown rice for a rice source. In some embodiments, the wet rice is milled (e.g., ground, chopped, crushed, mixed, pulverized, broken into smaller particle to expose the starch, etc.) to form a milled rice slurry.

In some embodiments, the milled slurry is agitated with an alpha-amylase enzyme until a mixture of dissolved maltodextrin and suspended protein is formed. In some embodiments, the maltodextrin is homogenized with the suspended protein to form a homogenous mixture. In some embodiments, the protein and maltodextrin are separated. In some embodiments, the protein and maltodextrin are separated using one or more of a filter press, decanter centrifuge, vibrating screen filter, inclined screen filter, or a microfiltration membrane. In some embodiments, $CaCl_2$) is added to the slurry. In some embodiments, the slurry is heated to a temperature between about 145° F. to about 210° F. In some embodiments, the mixture of dissolved maltodextrin and suspended starch is cooled to a temperature between about 140° F. and about 195° F. prior to homogenizing.

In some embodiments, the maltodextrin is exposed to a glucoamylase enzyme to form a rice syrup. In some embodiments, the enzyme comprises amigase mega L, or the like). In some embodiments, the treatment is carried out until the resulting rice syrup product has a DE of between about 43 and about 65 and up to 98. In some embodiments, the rice syrup is passed through a resin bed deionizer.

In some embodiments, the protein with is treated with a protease. In some embodiments, the protease is a DSM BAP protease. In some embodiments, the protein is treated with protease at a temperature ranging between about 135° F. and about 140° F.

In some embodiments, the method of manufacturing maltodextrin and protein from grain rice, the method comprises removing husks from rice to prepare de-husked rice by subjecting the rice to a husk breaker. In some embodiments, bran is removed from the de-husked rice to prepare whitened rice by subjecting the rice to treatment by a whitener machine. In some embodiments, the whitened rice is treated with water to prepare wet rice. In some embodiments, the wet rice is milled to form a milled rice slurry. In some embodiments, the slurry is agitated with an alpha-amylase enzyme until a mixture of dissolved maltodextrin and suspended protein is formed. In some embodiments, the maltodextrin and suspended protein is homogenized to form a homogenous mixture. In some embodiments, the protein and maltodextrin are separated from each other using a filter press or a microfiltration membrane. In some embodiments, $CaCl_2$) is added to the slurry. In some embodiments, the slurry is heated to a temperature between about 185° F. to about 195° F. In some embodiments, the mixture of dissolved maltodextrin and suspended starch is cooled to a temperature between about 160° F. and about 175° F. prior to homogenizing. In some embodiments, the maltodextrin is treated with a glucoamylase enzyme to form a rice syrup. In some embodiments, the rice syrup product has a DE of between about 43 and about 65 and up to 98. In some embodiments, the rice syrup is passed through an activated carbon column, and/or ultrafilter, and/or nanofilter to decolor and deproteinate, and/or process through a resin bed deionizer. In some embodiments, the protein is treated with a protease enzyme. In some embodiments, the protein is treated with a protease at a temperature ranging between about 110° F. and about 175° F.

Some embodiments, pertain to a system for manufacturing maltodextrin and protein from grain rice. In some embodiments, the system comprises a hold tank configured to receive rice. In some embodiments, the system comprises a steep tank comprising an agitator, wherein the steep tank is in thermal communication with a heat source configured to heat the contents of the steep tank. In some embodiments the milled rice slurry is heated with a steam injected jet cooker to enhance the rate of conversion of starch to maltodextrin. In some embodiments, the system comprises a colloid mill. In some embodiments, the system comprises a processor tank. In some embodiments, the system comprises a homogenizer. In some embodiments, the system comprises a filter press configured to separate an insoluble protein fraction from a dissolved maltodextrin solution.

In some embodiments, the system comprises a microfilter and/or ultrafilter membrane diafiltration system configured to separate an insoluble protein from dissolved maltodextrin. In some embodiments, the system comprises a centrifugal decanter with rinsing system configured to separate an insoluble protein from dissolved maltodextrin. In some embodiments, the system comprises a vibrating screen filter or an incline screen filter with rinsing system configured to separate an insoluble protein from dissolved maltodextrin. In some embodiments a combination of one or more of the aforementioned technologies can be made to separate an insoluble protein from dissolved maltodextrin.

BRIEF DESCRIPTION OF THE DRAWINGS

FIGS. 1A-1B show embodiments of rice syrup compositions prepared using the embodiments of the methods disclosed herein.

FIG. 6 shows an embodiment of a protein isolate prepared using an embodiment of a method disclosed herein.

DETAILED DESCRIPTION

Figure 2:
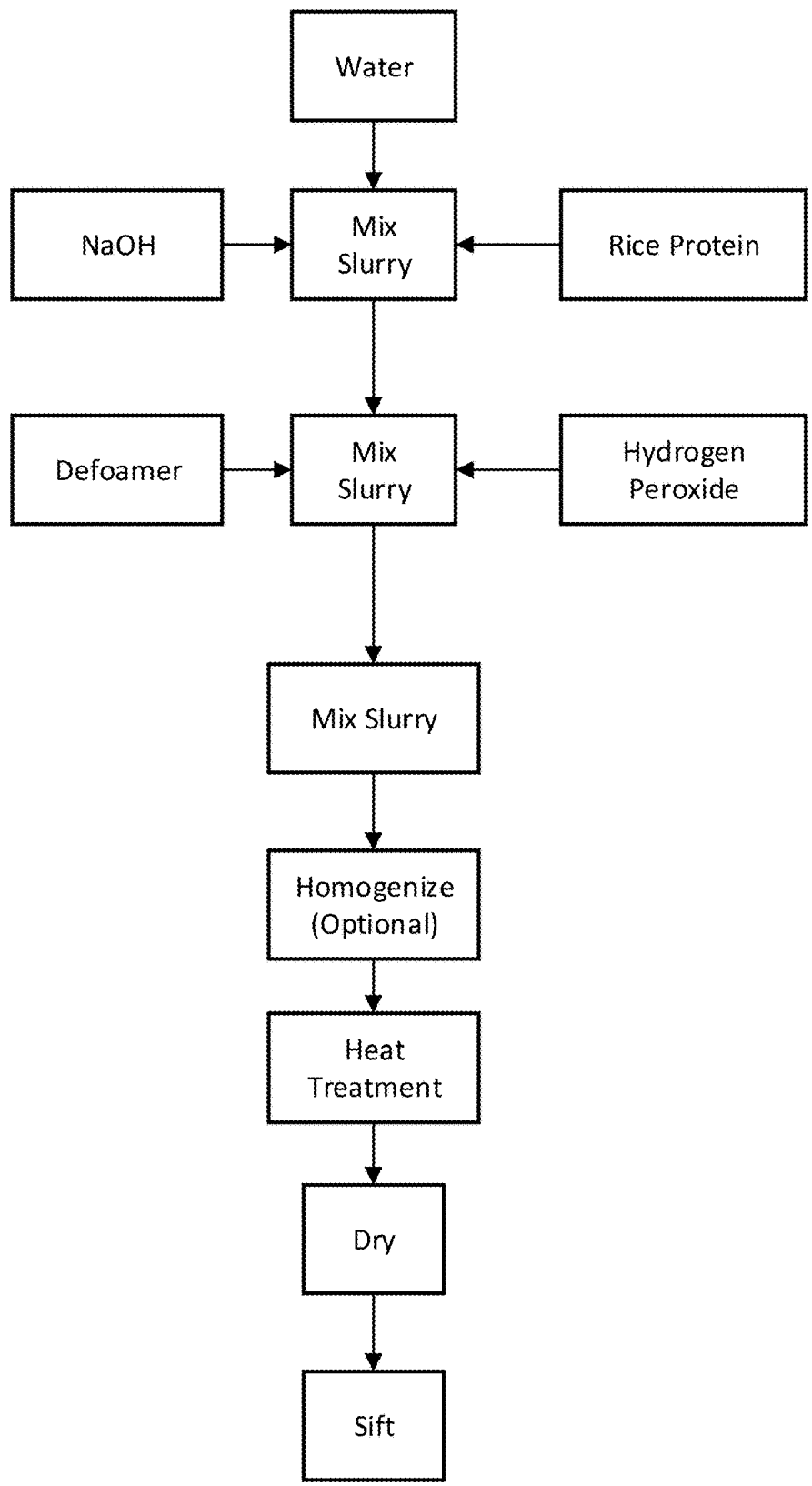
FIG. 2 is a flow chart outlining an embodiment of a method for preparing a rice protein.

Some embodiments described herein pertain to processes for preparing various plant-based food products, including rice. Some embodiments pertain to a process that allows the isolation, purification, and/or further processing of both starch and protein fractions from rice. In some embodiments, the starting material is from paddy rice raw material or white rice/white rice brokens. In some embodiments, maltodextrin and protein fractions are isolated from the rice starting materials. In some embodiments, rice syrup and protein isolate can be prepared. Some embodiments pertain to a process for the large scale manufacture of rice protein isolate and rice syrup products of variable dextrose equivalents (DE). Some embodiments of the process steps are described herein. Some embodiments pertain to a manufacturing facility for rice protein and rice starch products. It should be understood that steps can be added or left out to achieve one or more desired improvements. Certain features that are described in this disclosure in the context of separate implementations those features can also be implemented in combination in a single implementation (e.g., a combination of processes). Conversely, various features that are described in the context of a single implementation also can be implemented in multiple implementations separately or in any suitable subcombination and in different ordering. Also disclosed are various pieces of equipment associated with the aforementioned process. Those pieces of equipment may also be switched with other pieces of equipment that achieve the same result. While several embodiments are disclosed with respect to rice and oat products, it should be understood, in some embodiments, the methods disclosed herein are applicable to plant products and grains more generally, including but not limited to flaxseed, coconut, pumpkin, hemp, pea, chia, lentil, fava, potato, sunflower, quinoa, amaranth, oat, wheat, or combinations thereof.

Embodiments for Isolating Grain Maltodextrin and Proteins

In some embodiments, a process for converting raw paddy rice, brown rice, white rice, and/or rice brokens (e.g., white rice brokens) into rice maltodextrin, rice syrup, and rice proteins (e.g., peptides, oligopeptides, and amino acids) is provided. In some embodiments, rice starch (e.g., white rice starch) is converted enzymatically into maltodextrin. In some embodiments, after enzymatic conversion, the reaction mixture is separated into a protein stream and a maltodextrin stream. In some embodiments, the protein stream is purified and spray dried into a protein isolate product. In some embodiments, the enzymatic conversion of maltodextrin produces high dextrose equivalent (DE). In some embodiments, the rice syrup product has a DE of at least about 43 and up to less than or equal to 65 dextrose equivalent and up to less than or equal to 98 dextrose equivalent. In some embodiments, the rice syrup is decolorized and deproteinated through activated charcoal, and/or ultrafiltration, and/or nanofiltration, and deionized through resin bed deionizer. The rice syrup is concentrated via reverse osmosis and evaporation to about 80° brix and then packaged. In some embodiments, the protein from the protein stream is further processed to provide various protein mixtures. The methods described herein comprise one or more steps. In some embodiments, one or more steps disclosed herein can be excluded. In some embodiments, disclosed steps can be re-ordered and steps from one embodiment can be substituted or added to steps for another embodiment.

In some embodiments, to perform one or more of the methods disclosed herein, paddy rice is subjected to milling and is used (e.g., without de-husking, de-stoning, etc.). In other embodiments, paddy rice material is prepared for enzymatic treatment prior to use by performing one or more of the following steps: removal of husk; removal of bran to produce white rice product for further processing, heat treating the bran to stabilize the lipase degradation of the rice oil, pressing the oil from the bran for crude rice oil product, and/or packaging the stabilized rice bran product, and/or extracting the rice bran protein and or other nutritive materials from the stabilized bran. In some embodiments, prior to or after de-husking, the large impurities are removed by screening and sieving. In some embodiments, smaller impurities are removed by smaller successively smaller screens. In some embodiments, the screened paddy rice is then destoned with a destoning machine (which removes materials that deviates from the size of the grain kernel like straw, strings, small seeds, insect eggs, which are light and effectively extracted by sieving and then de-stoning to remove stones). In some embodiments, the destoned paddy rice is treated using a husk breaker. In some embodiments, from the husk breaker the material transferred to a separator where the husk and rice are separated. In some embodiments, the separated husk is blown away from the de-husked rice to a container (e.g., a bin) for collection and disposal.

In some embodiments, the de-husked brown rice is treated with an aspirator to remove residual fine husk particles and dust. In some embodiments, the brown rice is transferred to a series of whitener machines that remove and collect the bran. In some embodiments, the bran layer can be removed by abrasion. In some embodiments, the whitening is carried out by abrasive rollers (e.g., ones that are maintained substantially vertically) in the adjustable screen chamber using a whitening machine. In some embodiments, the whitening machine is provided with blowers to create a negative pressure. In some embodiments, the kernels are subject to polishing. In some embodiments, the polishing is controlled by adjustable screen holding mechanism. In some embodiments, the white rice is blown or otherwise transferred to a collection bin. In some embodiments, the bran is sent to an oil press for oil extraction.

In some embodiments, the bran is collected, heat treated with an extruder or heat exchanger to deactivate the naturally occurring lipase enzyme, and is pressed through the oil screw press presses. In some embodiments, the pressed oil is collected for possible further processing and refining and/or packaged in drums for warehousing and sale. In some embodiments, the defatted bran is then pulverized, collected for possible further processing and/or packaged for warehousing and sale.

In some embodiments, after the bran is separated from brown rice the remaining white rice and/or rice brokens are processed to separate the protein from the starch. In other embodiments, paddy rice and/or de-husked (whole or pulverized) is used as the starting material for starch and protein separation (instead of white rice and/or rice brokens.).

In some embodiments, as an alternative to dry milled white rice/brokens, a white rice/brokens slurry using wet milling is provided. In some embodiments, rice is steeped in heated water (e.g., a temperature of equal to or at least about: 140° F., 150° F., 160° F., 170° F., 185° F., 195° F., 210° F., or ranges including and/or spanning the aforementioned values) for a period of time equal to or at least about: 15 minutes, 30 minutes, 60 minutes, or ranges including and/or spanning the aforementioned values. Steeping the rice in this manner allows it to swell becoming soft. In some embodiments, the steeped white rice/brokens can then be wet milled. In some embodiments, wet milling advantageously causes less wear on the surfaces of the equipment performing the size reduction. In some embodiments, the white rice/brokens are steeped under vigorous agitation. In some embodiments, prior to enzymatic treatment, steeped rice can pumped through colloid mills for reducing particle size. In some embodiments, the milling is a two stage process with a first course milling and then a fine colloid milling (such that the particle size of the wet solids is such that greater than 50% pass through a 60 mesh, 80 mesh, 100 mesh screen, a 150 mesh screen, a 200 mesh screen, or ranges spanning and/or including the aforementioned values).

In some embodiment, after milling (dry or wet) the average particle size of the rice is less than or equal to about: 200 μm, 180 μm, 150 μm, 110 μm, 100 μm, 80 μm, 50 μm, or ranges including and/or spanning the aforementioned values. In some embodiment, after milling (dry or wet) the average particle size of the rice ranges from about 80 to about 110 μm.

In some embodiments, water is added to a reaction vessel. In some embodiments, the water heated to a temperature of less than or equal to about: 140° F., 150° F. 160° F., 170° F., 185° F., 190° F., 195° F., 210° F., or ranges including and/or spanning the aforementioned values. In some embodiments the milled rice slurry is heated using a jacketed reaction vessel. In some embodiments the milled rice slurry is heated with a steam injected jet cooker. In some embodiments, the jet cooker enhances the rate of conversion of starch to maltodextrin. In some embodiments, sufficient rice (dry milled or wet milled) is added to the reaction vessel to provide a solution with a % solid amount that is less than or equal to about 10%, 15%, 20%, 28%, 30%, 32%, 45%, or ranges including and/or spanning the aforementioned values (where % solid is calculated by wt solids/(total weight of solid and liquid)×100%). In some embodiments, this % solid slurry provides a balance between viscosity and enzymatic conversion efficiency (e.g., of starch to maltodextrin).

In some embodiments, $CaCl_2$) is added to the heated water. In some embodiments, $CaCl_2$) (e.g., as a dry powder or as an aqueous solution) is added to provide a solution having a weight ratio % of dry $CaCl_2$) relative to the rice solids (e.g., dry solids) that is equal to or less than about: 1.5%, 1.0%, 0.5%, 0.25%, 0.11%, 0.1%, 0.05%, 0.025%, 0.01% or ranges including and/or spanning the aforementioned values. As used for additives, the weight ratio % is calculated relative to the weight of rice feed stock (e.g., the weight of the additive/weight rice feedstock×100%). For example, in this case, the dry $CaCl_2$/total feed stock dry rice solids weight×100%.

In some embodiments, a starch degrading enzyme is added to the heated water. In some embodiments, the enzyme is an α-amylase (e.g., DSM Maxamyl HT, and the like). In some embodiments, α-amylase is added to provide a solution having a weight ratio % of α-amylase relative to the dry rice solids (e.g., the rice feedstock) that is equal to or less than about: 1.5%, 1.0%, 0.5%, 0.2%, 0.163%, 0.11%, 0.1%, 0.05%, 0.025%, 0.01% or ranges including and/or spanning the aforementioned values.

In some embodiments, where $CaCl_2$) is added, the $CaCl_2$) is added before the enzyme and the rice and in other embodiments after. In some embodiments, the enzyme is added before the rice and in other embodiments after.

In some embodiments, the enzyme and rice material are mixed together for a period of at least about: 1 hour, 2 hours, 3 hours, 5 hours, 16 hours, or ranges including and/or spanning the aforementioned values. In some embodiments, the enzymatic degradation is performed with agitation. In some embodiments, the enzymatic degradation of the rice-based starting material is performed for a period of time sufficient to provide a liquefied starch. In some embodiments, the enzymatic degradation of the rice-based starting material is performed for a period of time sufficient to provide dextrose equivalents (DE) of greater than or equal to about: 7, 15, 23, 43, 65, 98, or ranges including and/or spanning the aforementioned values. In some embodiments, a conversion to about 30 DE is obtained which is close to 100% starch conversion to maltodextrin. This allows relatively high levels of separation from the protein while providing a maltodextrin feedstock that will be optimal for further conversion with glucoamylase enzyme to a higher DE conversion rice syrup between 43 DE and 65 DE and up to 98 DE. In some embodiments, the high temperature ensures a near sterile process stream lowering any potential problem from biological contamination in the process.

In some embodiments, after enzymatic treatment at elevated temperature, the resulting maltodextrin/protein mixture is cooled less than or equal to about: 140° F., 150° F., 160° F., 175° F., 185° F. or ranges including and/or spanning the aforementioned values. In some embodiments, cooling is achieved by pumping the mixture through a heat exchanger.

In some embodiments, the maltodextrin/protein slurry is then homogenized. In some embodiments, the maltodextrin/protein slurry is pumped through the two stage homogenizer. In some embodiments, the first stage of the homogenizer is performed using a pressure of equal to or at least about: 2500 psi, 2250 psi, 2000 psi, or ranges including and/or spanning the aforementioned values. In some embodiments, the second stage of the homogenizer is performed using a pressure of equal to or at least about: 1000 psi, 750 psi, 500 psi, or ranges including and/or spanning the aforementioned values.

In some embodiments, the maltodextrin and protein from the maltodextrin/protein slurry is separated. In some embodiments, the maltodextrin and protein are separated using a separation system which may include one or more decanters, microfiltration and/or ultrafiltration membrane systems, filter presses, vibrating screen filters, incline screen filters, or combinations thereof. For example, the maltodextrin is removed from the protein though a series of decanter washes and/or solids resuspension and then re-decantation (when employing the decanter), through the introduction of diafiltration water (if employing the microfiltration (MF) and/or ultrafiltration (UF) technology), or through pressurized wash flushes (if employing the filter press systems), or re-suspension of filtered solids or water sprayed onto the solids while in the screen filter device. In some embodiments, the resulting protein solution can be collected for drying or for further processing. In some embodiments, the maltodextrin solution fraction is collected for drying or for further processing. In some embodiments, the process for separation removes protein, fat, and ash from the maltodextrin product at an efficiency (e.g., percent reduction) of greater than or equal to about: 95%, 98%, 99%, 99.5%, or ranges spanning and/or including the aforementioned values. In some embodiments, the process for separation removes maltodextrin from the protein product at an efficiency (e.g., percent reduction) of greater than or equal to about: 45%, 60%, 80%, 95%, 98%, 99%, 99.5%, or ranges spanning and/or including the aforementioned values. If maltodextrin is not almost completely removed, the protein product will not achieve the protein product purity level of >80%, and if the protein is not completely removed from the maltodextrin, the maltodextrin-based product will not meet the 0.5% maximum protein concentration specification for this product.

Maltodextrin Fraction

In some embodiments, the maltodextrin solution fraction is cooled to a temperature of less than or equal to about: 140° F., 150° F., 160° F., 170° F., 180°, 185° F. or ranges including and/or spanning the aforementioned values. In some embodiments, the maltodextrin solution fraction can be concentrated to 20% total solids. In some embodiments, the maltodextrin solution is concentrated using, for example, Reverse Osmosis (RO) membranes, a Thermal Vapor Recompression evaporator, a Mechanical Vapor Recompression (MVR) evaporator, through multi-effect evaporation, or the like. In some embodiments, the concentrated maltodextrin solution is concentrated to 35-60% total solids in by, for example, the evaporator.

In some embodiments, a dilute or concentrated maltodextrin fraction is subjected to conditions for saccharification. In some embodiments, the maltodextrin solution is treated with a glucoamylase enzyme. In some embodiments, sufficient glucoamylase is added to provide a solution having a weight ratio % of glucoamylase relative to the dry maltodextrin solids that is equal to or less than about: 1.5%, 1%, 0.5%, 0.1%, 0.05%, 0.025%, 0.1%, or ranges including and/or spanning the aforementioned values. In some embodiments, the glucoamylase enzyme is added under vigorous agitation to the dilute or concentrated maltodextrin solution.

In some embodiments, the glucoamylase treatment is performed for a period of a period of time equal to or at least about: 15 minutes, 30 minutes, 60 minutes, 90 minutes, 120 minutes, 960 minutes, or ranges including and/or spanning the aforementioned values. In some embodiments, the pH of the enzymatic treatment is adjusted to be equal to or at least about: 3.0, 3.5, 5.0, 5.8, 6.0, 7.0, or ranges including and/or spanning the aforementioned values. In some embodiments, the pH is adjusted by adding one or more of hydrochloric acid, citric acid, sodium hydroxide, or potassium hydroxide. In some embodiments, the base is adjusted using NaOH (e.g., in aqueous solution at 50% NaOH concentration). In some embodiments, the solution is held for the appropriate time for the high DE conversion (e.g., equal to or at least about: 43 DE, 65 DE, 98 DE, etc., or ranges spanning and/or including the aforementioned values).

In some embodiments, the converted syrup solution is heated (e.g., by pumping through a heat exchanger) to heat the syrup to equal to or at least about: 185° F., 195° F., 205° F., 210° F. or ranges including and/or spanning the aforementioned values. In some embodiments, this heating is performed for a period of time equal to or at least about: 5 minutes, 10 minutes, 20 minutes, or ranges including and/or spanning the aforementioned values. In some embodiments, this heating denatures and inactivates the glucoamylase enzyme.

In some embodiments, the stabilized syrup (where the glucoamylase has been deactivated) can be further treated. In some embodiments, the stabilized solution is passed through an evaporator at up to 60% solids followed by activated charcoal, and/or UF, and or nanofiltration (NF), and/or a combination of the aforementioned, and deionization system followed then again through an evaporator to increase solids and then followed by the deionization system. In some embodiments, the deionization system and process is configured to reduce ash content in the syrup by equal to or at least about: 95%, 98%, 99%, 99.5%, or ranges including and/or spanning the aforementioned values. In some embodiments, the deionized syrup is concentrated (e.g., in an evaporator) to a brix level of equal to or at least about: 50°, 60°, 70°, 80°, or ranges including and/or spanning the aforementioned values. In some embodiments, the syrup is then pasteurized. In some embodiments, the syrup is packaged using a packaging system where the syrup is pasteurized and hot packed and cooled thereafter.

Syrup Product

In some embodiments, a rice-derived carbohydrate product is provided. In some embodiments, the carbohydrate product is derived from a brown rice. FIGS. 1A and 1B provide profiles for embodiments of syrups made using a method as disclosed herein.

In some embodiments, each gram of the total solids in the syrup product comprises glucose in an amount (in g) equal to or greater than about: 0.90, 0.75, 0.60, 0.50, 0.35, 0.25, 0.15, 0.07, or ranges including and/or spanning the aforementioned values. In some embodiments, the weight percent of glucose relative to the total solids in the syrup product is equal to or greater than about: 90%, 75%, 60%, 50%, 35%, 25%, 15%, 7%, or ranges including and/or spanning the aforementioned values. In some embodiments, each gram of the total solids in the syrup product comprises maltose in an amount (in g) equal to or greater than about: 0.35, 0.30, 0.25, 0.20, 0.15, 0.05, or ranges including and/or spanning the aforementioned values. In some embodiments, the weight percent of maltose relative to the total solids in the syrup product is equal to or greater than about: 35%, 30%, 25%, 20%, 15%, 5%, or ranges including and/or spanning the aforementioned values. In some embodiments, each gram of the total solids in the syrup product comprises total mono and di-saccharide sugars (e.g., maltose and glucose) in an amount (in g) equal to or greater than about: 0.95, 0.80, 0.60, 0.50, 0.35, 0.25, 0.15, 0.05, or ranges including and/or spanning the aforementioned values. In some embodiments, the weight percent of mono and di-saccharide sugars relative to the total solids in the syrup product is equal to or greater than about: 95%, 80%, 60%, 50%, 35%, 25%, 15%, 5%, or ranges including and/or spanning the aforementioned values. In some embodiments, DE of the syrup is greater than or equal to about: 10, 15, 25, 35, 45, 50, 60, 70, 75, 85, 90, 99, or ranges including and/or spanning the aforementioned values. In some embodiments, the wt % solids in the syrup is equal to or greater than about: 85%, 80%, 75%, 60%, 50%, 40%, 30%, 20%, 15%, 5%, or ranges including and/or spanning the aforementioned values.

Protein Fraction

In some embodiments, the protein fraction is dried and isolated as a powder. In some embodiments, the protein fraction is further processed to provide additional protein products. In some embodiments, one or more of the following methods can be performed using the protein fraction as-is directly after separation from the maltodextrin fraction. In some embodiments, one or more of the following methods can be performed using the protein fraction isolated from the maltodextrin after the fraction has been diluted or concentrated to achieve a desired % solids mixture (as disclosed elsewhere herein). In some embodiments, one or more of the following methods can be performed using the powdered protein fraction product.

Hydrolyzed Protein Product

Some embodiments disclosed herein pertain to rice protein products for primary use in the meat analog replacer and extender food market. In some embodiments, this product is functional, nutritious, and free of allergens. Unlike soy protein extraction, some embodiments of the products disclosed herein are manufactured by a hexane-free process. Advantageously, some embodiments of this product are truly natural and can be organically certified. In some embodiments, the method uses powdered protein from brown rice isolated from the rice. In some embodiments, the rice protein starting material is isolated from maltodextrin as disclosed elsewhere herein. In some embodiments, the powder is processed to develop a smoother more soluble brown rice protein additive. In some embodiments, the powder advantageously stays in suspension better than traditional rice proteins. In some embodiments, the process steps and the equipment associated with the disclosed methods are described. One or more of the steps and pieces of equipment can be omitted. Additionally, processes and steps detailed for other rice products herein can be mixed and matched.

In some embodiments, as shown in FIG. 2, the process for producing a rice protein product includes one or more of the following steps. In some embodiments, brown rice protein powder is hydrated by adding to water (as disclosed elsewhere herein). In some embodiments, weight percent (wt %) of protein in the solution (e.g., dry weight rice protein/total solution weight×100%) is equal to or at least about: 40%, 35%, 30%, 25%, 20%, 15%, 10%, 5%, or ranges including and/or spanning the aforementioned values. In some embodiments, the (organic) rice protein powder is added to the water using a recirculating shear pump blender or other powder blending equipment.

In some embodiments, the water is heated to a temperature of equal to or at least about: 120° F., 130° F., 135° F., 140° F., 145° F., 150° F., 160° F., or ranges including and/or spanning the aforementioned values. In some embodiments, the hydrating process involves stirring the protein in water for a period of time equal to or at least about: 10 minutes, 30 minutes, 60 minutes, or ranges including and/or spanning the aforementioned values.

In some embodiments, the pH of the hydrated rice powder is adjusted with a base. In some embodiments, the pH is adjusted to be equal to or at least about: 8.0, 9.0, 9.5, 10.0, 10.5, or ranges including and/or spanning the aforementioned values. In some embodiments, the pH is adjusted by adding one or more of sodium hydroxide or potassium hydroxide. In some embodiments, the base is adjusted using NaOH (e.g., in aqueous solution at 10%, 25% 35%, 50% NaOH concentration or adding solid NaOH to the aqueous solution to achieve desired pH). In some embodiments, the protein is subjected to basic treatment for a period of time equal to or at least about: 30 minutes, 60 minutes, 90 minutes, or ranges including and/or spanning the aforementioned values. In some embodiments, the treatment with NaOH results in a hydrolyzed protein product solution.

In some embodiments, a de-foamer is added to the hydrolyzed protein product solution. In some embodiments, de-foamer is added to provide a solution having a weight ratio % of de-foamer to dry weight solids that is equal to or less than about: 0.1%, 0.05%, 0.01%, 0.005%, 0.0025%, 0.001%, or ranges including and/or spanning the aforementioned values. In some embodiments, the de-foamer is a food grade de-foaming agent (e.g., one or more of Magrabar Organic 3000 de-foamer, Organic 3300, or the like). In some embodiments, the de-foamer is an organically certifiable de-foamer. In some embodiments, a solution of hydrogen peroxide is added to the solution. In some embodiments, hydrogen peroxide is added to provide a solution having a weight ratio % of 50% hydrogen peroxide solution to dry weight solids that is equal to or less than about: 0.5%, 0.1%, 0.05%, 0.01%, or ranges including and/or spanning the aforementioned values. In some embodiments, the de-foamer and/or hydrogen peroxide containing protein solution is allowed to agitate for a period of time equal to or at least about: 10 minutes, 20 minutes, 30 minutes, 60 minutes, or ranges including and/or spanning the aforementioned values.

In some embodiments, the modified hydrolyzed protein product can be homogenized using a homogenizer. In some embodiments, the homogenization process is performed until a desired viscosity is reached (e.g., equal to or less than about: 10000 cP, 5000 cP, 1000 cP, 500 cP, 100 cP, 5 cP, or ranges including and/or spanning the aforementioned values). In some embodiments, the homogenizer is operated at a pressure of equal to or at least about: 2500 psi, 2250 psi, 2000 psi, 1000 psi, 750 psi, 500 psi, or ranges including and/or spanning the aforementioned values. In some embodiments, the hydrolyzed protein product is homogenized in a 2-stage homogenizer. In some embodiments, the first stage of the homogenizer is performed using a pressure of equal to or at least about: 2500 psi, 2250 psi, 2000 psi, or ranges including and/or spanning the aforementioned values. In some embodiments, the second stage of the homogenizer is performed using a pressure of equal to or at least about: 1000 psi, 750 psi, 500 psi, or ranges including and/or spanning the aforementioned values. In some embodiments, the homogenization process is performed for a period of time equal to or at least about: 30 minutes, 60 minutes, 120 minutes, 180 minutes, or ranges including and/or spanning the aforementioned values.

In some embodiments, the protein solution is then heated to a temperature of greater than or equal to about: 190° F., 195° F., 200° F., or ranges including and/or spanning the aforementioned values. This heating step can kill microbes present in the product preventing any microbial infection that might have occurred during the processing and transfer of the protein solution. In some embodiments, the rice solution is then spray-dried in a tall form dryer. In some embodiments, the drying process is conducted at a temperature of greater than or at least about: 350° F., 410° F., 450° F., 510° F., or ranges including and/or spanning the aforementioned values.

In some embodiments, the dried powder is sifted and run through a metal detector and then bagged for warehousing. In some embodiments, the dried protein product powder is subjected to one or more of the following: sifting through a 40 mesh sifter, checked for metal shavings through a magnetic metal detector, bagged in 20 kg bags or totes with appropriate product and tracking labels attached, and then sent to warehousing until ready to ship.

A flow diagram outlining an embodiment of the method of preparing the rice protein disclosed in this section is provided in FIG. 2. In some embodiments, the protein product is advantageously smoother product and suspendable product than available rice protein products. In some embodiments, the protein product remains suspended in water for longer periods than available rice protein products. In some embodiments, upon mixing about 20 g of the protein product in 12 fluid ounces of water, the product remains in suspension without visible and/or measurable sedimentation for a period of equal to or at least about: 15 minutes, 30 minutes, 60 minutes, 120 minutes, or ranges including and/or spanning the aforementioned values. In some embodiments, upon mixing about 20 g of the protein product in 12 fluid ounces of water, the product remains in suspension without visible and/or measurable sedimentation for a period of equal to or at least about: a week, a month, two months, six months, or ranges including and/or spanning the aforementioned values.

Enzymatic Treatment of Protein Fraction

In some embodiments, the separated rice protein fraction is further treated enzymatically. In some embodiments, this additional treatment step advantageously improves the solubility and suspendability of the rice protein isolate. In some embodiments, the protein slurry fraction is heated to a temperature of equal to or at least about: 120° F., 135° F., 140° F., 150° F., 160° F., or ranges including and/or spanning the aforementioned values. In some embodiments, the protein fraction is brought to the aforementioned temperatures by mixing it with additional water adjusted to the appropriate a set point temperature on a mixing valve. In some embodiments, the protein fraction is diluted or concentrated to a total solids percent of equal to or at least about: 5%, 10%, 15%, 17%, 20%, or ranges or ranges including and/or spanning the aforementioned values.

In some embodiments, the enzyme treatment is performed at an alkaline pH. In some embodiments, the protein slurry pH is adjusted to equal to or at least about: 3.0, 4.0, 5.0, 6.0, 7.9, 8.3, 9.0, 9.5, or ranges including and/or spanning the aforementioned values. In some embodiments, the pH is adjusted with NaOH, HCl, or citric acid. In some embodiments, the enzyme used to treat the protein fraction is a protease. In some embodiments, the enzyme used to treat the protein fraction is an alkaline protease, a neutral protease, an acid protease, or combinations thereof. In some embodiments, the protease is a endoprotease (e.g., a serine endoprotease). In some embodiments, the protease is an exoprotease. In some embodiments, the protease is selected from the group consisting of DSM BAP, DSM FPC, DSM CPP, DSM AFP, Enzeco Fungal 400, Enzeco BL, Enzeco Fungal Acid, and the like. In some embodiments, the weight ratio % of protease added relative to the amount of protein solids is less than or equal to about: 0.01%, 0.05%, 0.1%, 0.5%, 1.0%, 2.1%, or ranges including and/or spanning the aforementioned values. In some embodiments, enzyme is mixed with the protein fraction for a period of time equal to or at least about: 15 minutes, 30 minutes, 60 minutes, or ranges including and/or spanning the aforementioned values. In some embodiments, the enzymatic treatment of the protein fraction is performed at a temperature of less than or equal to about: 120° F., 130° F., 135° F., 140° F., 150° F., 160° F., or ranges including and/or spanning the aforementioned values.

In some embodiments, after about the hold time at temperature, the modified protein is heated (e.g., pumped through a heat exchanger) to temperature of greater than or equal to about: 185° F., 190° F., 195° F., 200° F., 210° F., or ranges including and/or spanning the aforementioned values. In some embodiments, once this temperature is reached it is held for a period of at least about: 5 minutes, 1 minute, 10 seconds, or ranges including and/or spanning the aforementioned values. In some embodiments, this elevated temperature denatures the enzyme.

In some embodiments, the protein slurry is dried (e.g., by a tall form or box spray dryer). In some embodiments, the resulting enzymatically treated protein is a powder. In some embodiments, the powder is dried to a moisture content by weight of less than or equal to about: 3%, 4%, 5%, 6%, or ranges including and/or spanning the aforementioned values. In some embodiments, the drier is fitted with a high pressure nozzle atomizer. In some embodiments, the atomizing nozzle pressures are maintained at about 3,000-4,000 psi with drier inlet temperatures of about 450-550° F. and exhaust temperatures of about 180-200° F.

In some embodiments, as the protein powder is transferred through a vibratory separator to discharge larger particles and the through a magnet (e.g., rare earth) to remove any metal.

Embodiment of Enzymatically Treated Protein Product

Some embodiments disclosed herein pertain to a suspension grade, clean label, non-GMO, enzymatically hydrolyzed rice protein product (e.g., brown rice protein product). In some embodiments, the hydrolyzed rice protein product is for use in the beverage and related food protein ingredient market (and other uses). In some embodiments, the hydrolyzed rice protein product is manufactured with a hexane-free process. In some embodiments, a brown rice protein fraction (powder or suspended) isolated from the starch fraction of rice is enzymatically hydrolyzed to provide a grit-free, smoother, brown rice protein additive that stays in suspension better than available rice proteins. In some embodiments, embodiments of the process steps and the equipment associated with the aforementioned process are described. One or more of the steps and pieces of equipment can be omitted. Additionally, processes and steps detailed for other rice products herein can be mixed and matched.

Figure 3:
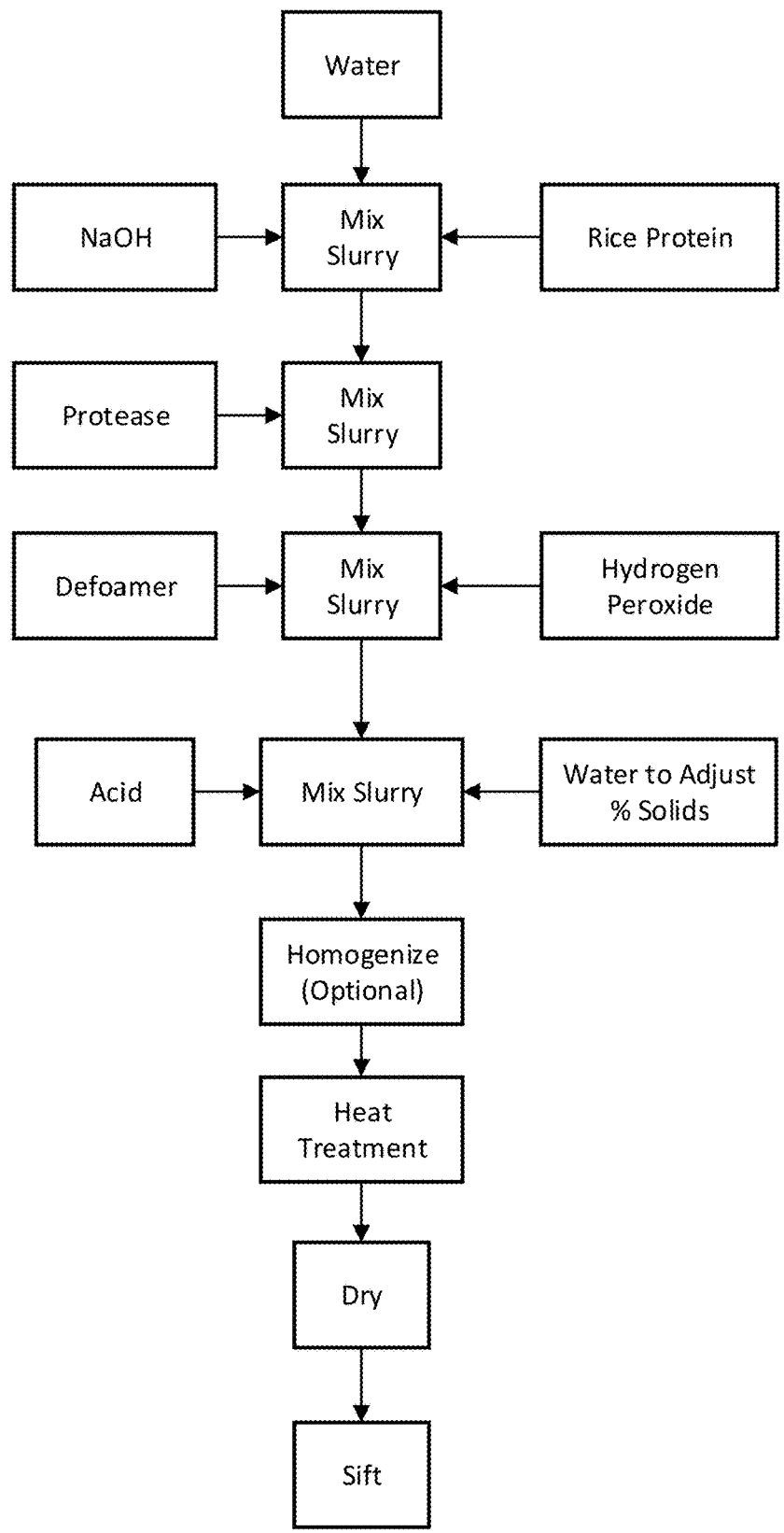
FIG. 3 is a flow chart outlining an embodiment of a method for preparing an embodiment a rice protein.

In some embodiments, as shown in FIG. 3, the process for producing the treated protein product includes one or more of the following steps. In some embodiments, brown rice protein powder is hydrated by adding to water (as disclosed elsewhere herein). In some embodiments, weight percent of protein in the solution (e.g., dry weight rice protein/total solution weight×100%) is equal to or at least about: 40%, 35%, 30%, 25%, 20%, 15%, or ranges including and/or spanning the aforementioned values. In some embodiments, the (organic) rice protein powder is added to the water using a recirculating shear pump blender or other powder blending equipment.

In some embodiments, the water is heated to a temperature of equal to or at least about: 120° F., 130° F., 135° F., 140° F., 145° F., 150° F., 160° F., 170° F., 180° F., 190° F., or ranges including and/or spanning the aforementioned values. In some embodiments, the hydrating process involves stirring the protein in water for a period of time equal to or at least about: 10 minutes, 30 minutes, 60 minutes, or ranges including and/or spanning the aforementioned values.

In some embodiments, the pH of the hydrated rice powder is adjusted with a base. In some embodiments, the pH is adjusted to equal to or at least about: 3.0, 4.0, 5.0, 6.0, 7.0, 8.0, 9.0, 9.75, 10.0, 10.5, or ranges including and/or spanning the aforementioned values. In some embodiments, the pH is adjusted by adding one or more of sodium hydroxide or potassium hydroxide. In some embodiments, the base is adjusted using NaOH (e.g., in aqueous solution at 10%, 25%, 35%, 50% NaOH or KOH concentration or addition of solid base to the solution).

In some embodiments, when the pH is stabilized, an alkaline, neutral, acid protease, or combination thereof is added. In some embodiments, the enzyme used to treat the protein fraction is an alkaline, neutral, acid, or combination thereof protease. In some embodiments, the protease is a endoprotease (e.g., a serine endoprotease). In some embodiments, the protease is an exoprotease. In some embodiments, the protease is selected from the group consisting of DSM BAP, DSM FPC, DSM CPP, DSM AFP, Enzeco Fungal 400, Enzeco BL, Enzeco Fungal Acid, and the like. In some embodiments, the weight ratio % of added protease (relative to the of the dry rice protein weight) is less than or equal to about: 0.005%, 0.01%, 0.02%, 0.05%, 0.1%, 0.5%, 1.0%, or ranges including and/or spanning the aforementioned values. In some embodiments, enzyme is mixed with the protein for a period of time equal to or at least about: 15 minutes, 30 minutes, 60 minutes, or ranges including and/or spanning the aforementioned values. In some embodiments, the enzymatic treatment of the protein is performed at a temperature of less than or equal to about: 130° F., 135° F., 140° F., 150° F., 160° F., or ranges including and/or spanning the aforementioned values.

In some embodiments, a de-foamer is added to the hydrolyzed protein product solution. In some embodiments, de-foamer is added to provide a solution having a weight ratio % of de-foamer to dry weight solids that is equal to or less than about: 0.1%, 0.05%, 0.01%, 0.005%, 0.0025%, 0.001%, or ranges including and/or spanning the aforementioned values. In some embodiments, the de-foamer is a food grade de-foaming agent (e.g., one or more of Magrabar Organic 3000 de-foamer, Organic 3300, or the like). In some embodiments, the de-foamer is an organically certifiable de-foamer. In some embodiments, a solution of hydrogen peroxide is added to the solution. In some embodiments, hydrogen peroxide is added to provide a solution having a weight ratio % of 50% hydrogen peroxide solution to dry weight solids that is equal to or less than about: 0.5%, 0.1%, 0.05%, 0.01%, or ranges including and/or spanning the aforementioned values. In some embodiments, the de-foamer and/or hydrogen peroxide containing protein solution is allowed to agitate for a period of time equal to or at least about: 10 minutes, 20 minutes, 30 minutes, 60 minutes, or ranges including and/or spanning the aforementioned values.

In some embodiments, the pH of the treated protein is adjusted with an acid or a base. In some embodiments, the pH is adjusted to be equal to or at least about: 7.0, 7.5, 8.0, or ranges including and/or spanning the aforementioned values. In some embodiments, the pH is adjusted by adding one or more of an organic acid. In some embodiments, the organic acid is citric acid. In some embodiments, the pH is adjusted by adding a base such as NaOH or KOH.

In some embodiments, the modified hydrolyzed protein product can be homogenized using a homogenizer. In some embodiments, the homogenization process is performed until a desired viscosity is reached (e.g., equal to or less than about: 10000 cP, 5000 cP, 1000 cP, 500 cP, 100 cP, 5 cP, or ranges including and/or spanning the aforementioned values). In some embodiments, the homogenizer is operated at a pressure of equal to or at least about: 2500 psi, 2250 psi, 2000 psi, 1000 psi, 750 psi, 500 psi, or ranges including and/or spanning the aforementioned values. In some embodiments, the hydrolyzed protein product is homogenized in a 2-stage homogenizer. In some embodiments, the first stage of the homogenizer is performed using a pressure of equal to or at least about: 2500 psi, 2250 psi, 2000 psi, or ranges including and/or spanning the aforementioned values. In some embodiments, the second stage of the homogenizer is performed using a pressure of equal to or at least about: 1000 psi, 750 psi, 500 psi, or ranges including and/or spanning the aforementioned values. In some embodiments, the homogenization process is performed for a period of time equal to or at least about: 30 minutes, 60 minutes, 120 minutes, 180 minutes, or ranges including and/or spanning the aforementioned values.

In some embodiments, the protein solution is then heated to a temperature of greater than or equal to about: 190° F., 195° F., 200° F., 210° F., or ranges including and/or spanning the aforementioned values. In some embodiments, once this temperature is reached it is held for a period of at least about: 15 minutes, 10 minutes, 5 minutes, or ranges including and/or spanning the aforementioned values. This heating step can kill microbes present in the product preventing any microbial infection that might have occurred during the processing and transfer of the protein solution. In some embodiments, the rice solution is then spray-dried in a tall form dryer. In some embodiments, the drying process is conducted at a temperature of greater than or at least about: 350° F., 410° F., 450° F., 550° F., or ranges including and/or spanning the aforementioned values.

In some embodiments, the dried powder is sifted and run through a metal detector and then bagged for warehousing. In some embodiments, the dried protein product powder is subjected to one or more of the following: sifting through a 40 mesh sifter, checked for metal shavings through a magnetic metal detector, bagged in 20 kg bags or totes with appropriate product and tracking labels attached, and then sent to warehousing until ready to ship.

A flow diagram outlining an embodiment of the method of preparing the rice protein disclosed in this section is provided in FIG. 3.

In some embodiments, the protein product is advantageously smoother product and suspendable product than available rice protein products. In some embodiments, the protein product remains suspended in water for longer periods than available rice protein products. In some embodiments, upon mixing about 20 g of the protein product in 12 fluid ounces of water, the product remains in suspension without visible and/or measurable sedimentation for a period of equal to or at least about: 15 minutes, 30 minutes, 60 minutes, 120 minutes, or ranges including and/or spanning the aforementioned values. In some embodiments, upon mixing about 20 g of the protein product in 12 fluid ounces of water, the product remains in suspension without visible and/or measurable sedimentation for a period of equal to or at least about: a week, a month, two months, six months, or ranges including and/or spanning the aforementioned values.

Embodiment of Enzymatically Treated Protein Product

Some embodiments disclosed herein pertain to a enzymatically hydrolyzed rice protein product (e.g., brown rice protein product) for use in the extruded food market (and other uses). In some embodiments, the protein is an allergen-friendly high protein extrusion that are also vegan and clean label. Unlike traditional soy and whey protein extractions embodiments of the products disclosed herein are hexane free providing a truly natural chemical-free product. In some embodiments, the process starts with powdered rice protein that is enzymatically hydrolyzed to develop a smoother more soluble rice protein additive that stays in suspension better than traditional rice proteins. In some embodiments, embodiments of the process steps and the equipment associated with the aforementioned process are described. One or more of the steps and pieces of equipment can be omitted. Additionally, processes and steps detailed for other rice products herein can be mixed and matched.

Figure 4:
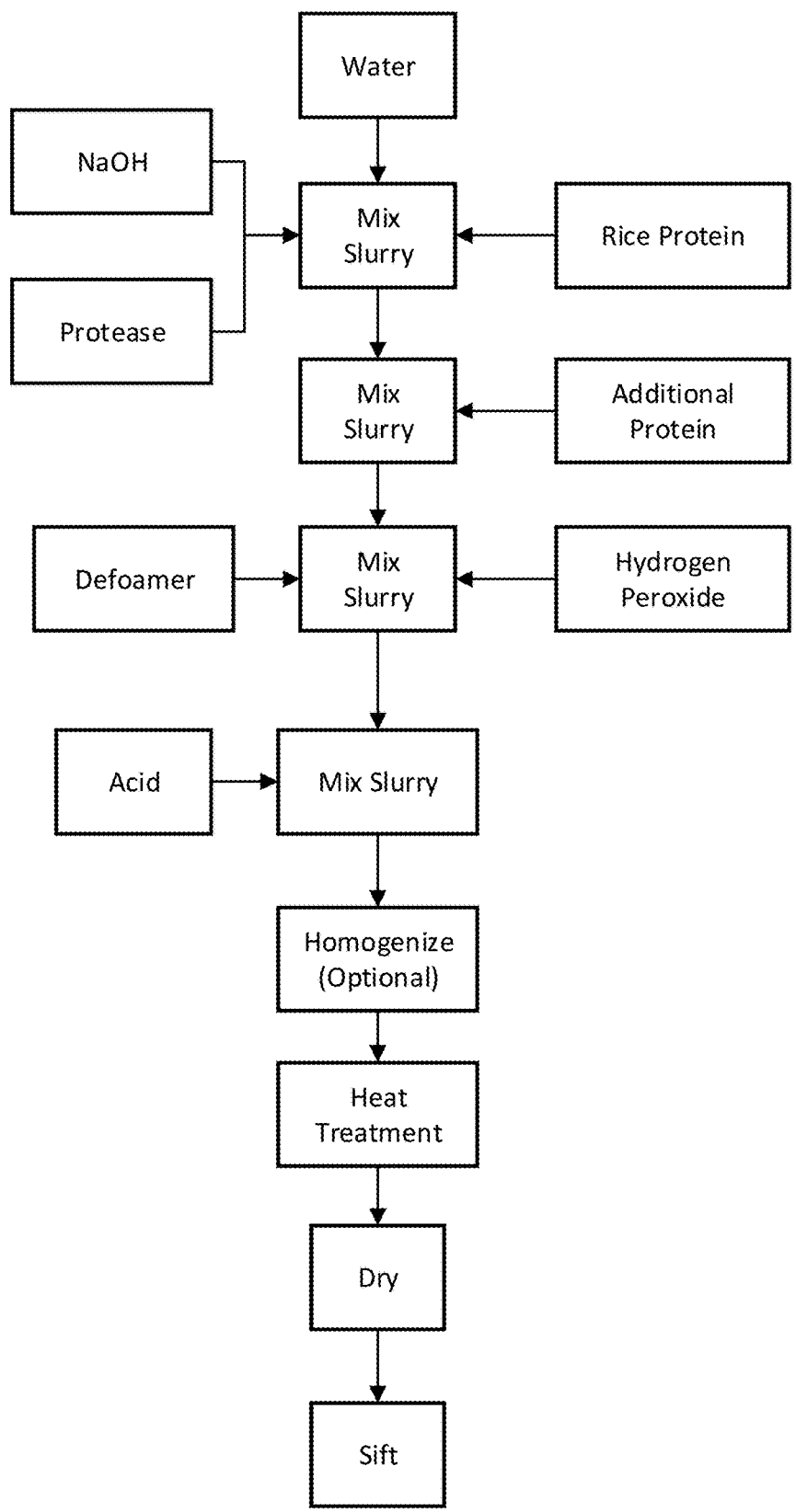
FIG. 4 is a flow chart outlining an embodiment of a method for preparing an embodiment a rice protein.

In some embodiments, as shown in FIG. 4, the process for producing the treated protein product includes one or more of the following steps. In some embodiments, brown rice protein powder is hydrated by adding to water (as disclosed elsewhere herein). In some embodiments, weight percent of protein in the solution (e.g., weight rice protein/total solution weight×100%) is equal to or at least about: 40%, 35%, 30%, 25%, 20%, 15%, 10%, 5%, or ranges including and/or spanning the aforementioned values. In some embodiments, the (organic) rice protein powder is added to the water using a recirculating shear pump blender or other powder blending equipment.

In some embodiments, the water is heated to a temperature of equal to or at least about: 120° F., 130° F., 135° F., 140° F., 145° F., 150° F., 160° F., 170° F., 180° F., 190° F., or ranges including and/or spanning the aforementioned values. In some embodiments, the hydrating process involves stirring the protein in water for a period of time equal to or at least about: 10 minutes, 30 minutes, 60 minutes, or ranges including and/or spanning the aforementioned values.

In some embodiments, the pH of the hydrated rice powder is adjusted with an acid or a base. In some embodiments, the pH is adjusted to equal to or at least about: 3.0, 4.0, 5.0, 6.0, 7.0, 8.0, 9.0, 9.75, 10.0, 10.5, or ranges including and/or spanning the aforementioned values. In some embodiments, the pH is adjusted by adding one or more of sodium hydroxide or potassium hydroxide, HCl or citric acid. In some embodiments, the base is adjusted using NaOH (e.g., in aqueous solution at 10%, 25%, 35%, 50% NaOH or KOH concentration or solid NaOH or KOH). In some embodiments the pH is adjusted with HCl or citric acid (e.g, in aqueous solution at 10%, 25%, 35%, 50% or with solid citric acid). In some embodiments, this pH is maintained throughout the enzymatic hydrolysis reaction.

In some embodiments, when the pH is stabilized at the target level, an alkaline, neutral, or acid protease is added. In some embodiments, the enzyme used to treat the protein fraction is an alkaline, neutral, or acid protease. In some embodiments, the protease is a endoprotease (e.g., a serine endoprotease). In some embodiments, the protease is an exoprotease. In some embodiments, the protease is selected from the group consisting of DSM BAP, DSM FPC, DSM CPP, DSM AFP, Enzeco Fungal 400, Enzeco BL, Enzeco Fungal Acid, and the like. In some embodiments, the weight ratio % percent of added protease (relative to the dry weight of the dry rice protein) is less than or equal to about: 0.005%, 0.01%, 0.02%, 0.05%, 0.1%, 0.5%, 1.0%, or ranges including and/or spanning the aforementioned values. In some embodiments, enzyme is mixed with the protein for a period of time equal to or at least about: 90 minutes, 120 minutes, 150 minutes, 180 minutes, or ranges including and/or spanning the aforementioned values. In some embodiments, a slight bitter taste should develop in this product from the enzyme hydrolysis. In some embodiments, the enzymatic treatment of the protein is performed at a temperature of less than or equal to about: 130° F., 135° F., 140° F., 150° F., 160° F., or ranges including and/or spanning the aforementioned values.

In some embodiments, after about 60 minutes (±30 minutes), an additional amount of untreated protein powder can be added to the solution for enzymatic treatment. In some embodiments, the added protein has a weight ratio % relative to the first dry weight protein addition of equal to or less than about: 5%, 10%, 25%, 50%, 75%, 100%, or ranges including and/or spanning the aforementioned values. In some embodiments, enzyme is mixed with the protein for a period of time equal to or at least about: 90 minutes, 120 minutes, 150 minutes, 180 minutes, or ranges including and/or spanning the aforementioned values.

In some embodiments, a de-foamer is added to the hydrolyzed protein product solution. In some embodiments, de-foamer is added to provide a solution having a weight ratio % of de-foamer to dry weight solids that is equal to or less than about: 0.1%, 0.05%, 0.01%, 0.005%, 0.0025%, 0.001%, or ranges including and/or spanning the aforementioned values. In some embodiments, the de-foamer is a food grade de-foaming agent (e.g., one or more of Magrabar Organic 3000 de-foamer, Organic 3300, or the like). In some embodiments, the de-foamer is an organically certifiable de-foamer. In some embodiments, a solution of hydrogen peroxide is added to the solution. In some embodiments, hydrogen peroxide is added to provide a solution having a weight ratio % of 50% hydrogen peroxide solution to dry weight solids that is equal to or less than about: 0.5%, 0.1%, 0.05%, 0.01%, or ranges including and/or spanning the aforementioned values. In some embodiments, the de-foamer and/or hydrogen peroxide containing protein solution is allowed to agitate for a period of time equal to or at least about: 10 minutes, 20 minutes, 30 minutes, 60 minutes, or ranges including and/or spanning the aforementioned values.

In some embodiments, the pH of the treated protein is adjusted with an acid. In some embodiments, the pH is adjusted to be equal to or at least about: 7.0, 7.5, 8.0, or ranges including and/or spanning the aforementioned values. In some embodiments, the pH is adjusted by adding one or more of an organic acid. In some embodiments, the organic acid is citric acid.

In some embodiments, the modified hydrolyzed protein product can be homogenized using a homogenizer. In some embodiments, the homogenization process is performed until a desired viscosity is reached (e.g., equal to or less than about: 10000 cP, 5000 cP, 1000 cP, 500 cP, 100 cP, 5 cP, or ranges including and/or spanning the aforementioned values). In some embodiments, the homogenizer is operated at a pressure of equal to or at least about: 2500 psi, 2250 psi, 2000 psi, 1000 psi, 750 psi, 500 psi, or ranges including and/or spanning the aforementioned values. In some embodiments, the hydrolyzed protein product is homogenized in a 2-stage homogenizer. In some embodiments, the first stage of the homogenizer is performed using a pressure of equal to or at least about: 2500 psi, 2250 psi, 2000 psi, or ranges including and/or spanning the aforementioned values. In some embodiments, the second stage of the homogenizer is performed using a pressure of equal to or at least about: 1000 psi, 750 psi, 500 psi, or ranges including and/or spanning the aforementioned values. In some embodiments, the homogenization process is performed for a period of time equal to or at least about: 30 minutes, 60 minutes, 120 minutes, 180 minutes, or ranges including and/or spanning the aforementioned values.

In some embodiments, the protein solution is then heated to a temperature of greater than or equal to about: 190° F., 195° F., 200° F., or ranges including and/or spanning the aforementioned values. In some embodiments, once this temperature is reached it is held for a period of at least about: 15 minutes, 10 minutes, 5 minutes, or ranges including and/or spanning the aforementioned values. This heating step can kill microbes present in the product preventing any microbial infection that might have occurred during the processing and transfer of the protein solution. In some embodiments, the rice solution is then spray-dried in a tall form dryer. In some embodiments, the drying process is conducted at a temperature of greater than or at least about: 350° F., 410° F., 450° F., 550° F. or ranges including and/or spanning the aforementioned values.

In some embodiments, the dried powder is sifted and run through a metal detector and then bagged for warehousing. In some embodiments, the dried protein product powder is subjected to one or more of the following: sifting through a 40 mesh sifter, checked for metal shavings through a magnetic metal detector, bagged in 20 kg bags or totes with appropriate product and tracking labels attached, and then sent to warehousing until ready to ship.

A flow diagram outlining an embodiment of the method of preparing the rice protein disclosed in this section is provided in FIG. 4.

In some embodiments, the protein product is advantageously smoother product and suspendable product than available rice protein products. In some embodiments, the protein product remains suspended in water for longer periods than available rice protein products. In some embodiments, upon mixing about 20 g of the protein product in 12 fluid ounces of water, the product remains in suspension without visible and/or measurable sedimentation for a period of equal to or at least about: 15 minutes, 30 minutes, 60 minutes, 120 minutes, or ranges including and/or spanning the aforementioned values. In some embodiments, upon mixing about 20 g of the protein product in 12 fluid ounces of water, the product remains in suspension without visible and/or measurable sedimentation for a period of equal to or at least about: a week, a month, two months, six months, or ranges including and/or spanning the aforementioned values.

Embodiment of Enzymatically Treated Protein Product

Some embodiments disclosed herein pertain a hydrolyzed brown rice protein product, for primary use in the chemical free flavor enhancement food market (and other uses). In some embodiments, the product has a substantially grit-free mouthfeel. In some embodiments, the product is a functional savory natural food unami flavor enhancer which is substantially allergen free. In some embodiments, the process starts with powdered rice protein (e.g., brown rice protein product) and hydrolyzes the protein enzymatically to develop a smoother more soluble rice protein additive that stays in suspension better than traditional brown rice proteins. In some embodiments, embodiments of the process steps and the equipment associated with the aforementioned process are described. One or more of the steps and pieces of equipment can be omitted. Additionally, processes and steps detailed for other rice products herein can be mixed and matched.

Figure 5:
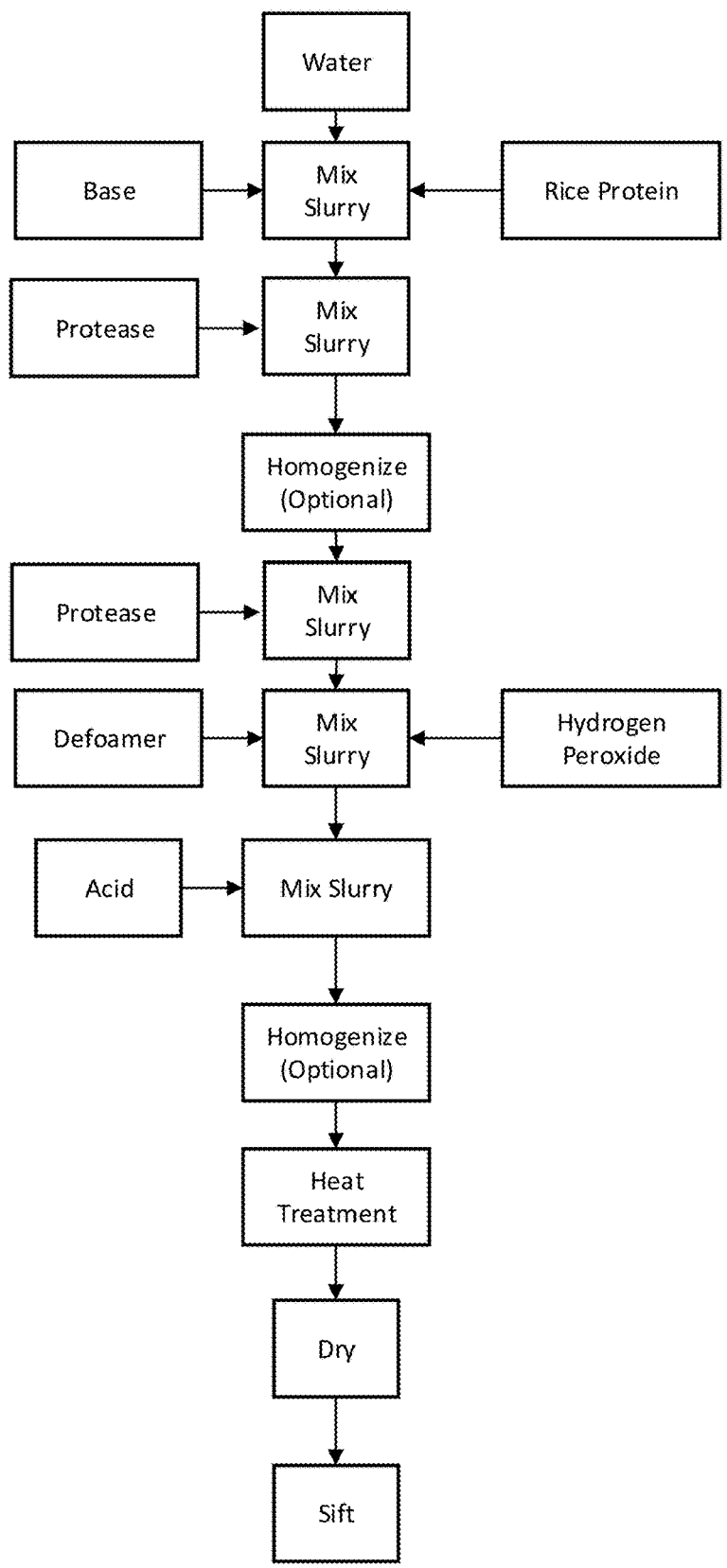
FIG. 5 is a flow chart outlining an embodiment of a method for preparing an embodiment a rice protein.

In some embodiments, as shown in FIG. 5, the process for producing the treated protein product includes one or more of the following steps. In some embodiments, brown rice protein powder is hydrated by adding to water (as disclosed elsewhere herein). In some embodiments, weight percent of protein in the solution (e.g., dry weight rice protein/total solution weight×100%) is equal to or at least about: 40%, 35%, 30%, 25%, 20%, 15%, 10%, 5%, or ranges including and/or spanning the aforementioned values. In some embodiments, the (organic) rice protein powder is added to the water using a recirculating shear pump blender or other powder blending equipment.

In some embodiments, the water is heated to a temperature of equal to or at least about: 110° F., 120° F., 130° F., 135° F., 140° F., 145° F., 150° F., 160° F., 180° F., 190° F., or ranges including and/or spanning the aforementioned values. In some embodiments, the hydrating process involves stirring the protein in water for a period of time equal to or at least about: 10 minutes, 30 minutes, 60 minutes, or ranges including and/or spanning the aforementioned values.

In some embodiments, the pH of the hydrated rice powder is adjusted with an acid or a base. In some embodiments, the pH is adjusted to equal to or at least about: 3.0, 4.0, 5.0, 6.0, 7.0, 8.0, 9.0, 9.75, 10.0, 10.5, or ranges including and/or spanning the aforementioned values. In some embodiments, the pH is adjusted by adding one or more of sodium hydroxide or potassium hydroxide. In some embodiments, the pH is adjusted using NaOH or KOH. In some embodiments, the pH is adjusted using HCl or citric acid (e.g., in aqueous solution at 10%, 25%, 35%, 50% HCl or citric acid solution concentration or solid citric acid)

In some embodiments, when the pH is stabilized, an alkaline, neutral, acid protease, or combination thereof is added. In some embodiments, the enzyme used to treat the protein fraction is an alkaline protease. In some embodiments, the protease is a endoprotease (e.g., a serine endoprotease). In some embodiments, the protease is an exoprotease. In some embodiments, the protease is selected from the group consisting of DSM BAP, DSM FPC, DSM CPP, DSM AFP, Enzeco Fungal 400, Enzeco BL, Enzeco Fungal Acid, and the like. In some embodiments, the weight ratio % of added protease (based on total dry protein weight) is less than or equal to about: 0.005%, 0.01%, 0.02%, 0.05%, 0.1%, 0.5%, 1.0%, or ranges including and/or spanning the aforementioned values. In some embodiments, the enzymatic treatment of the protein is performed at a temperature of less than or equal to about: 110° F., 120° F., 130° F., 135° F., 140° F., 145° F., 150° F., 160° F., or ranges including and/or spanning the aforementioned values. In some embodiments, enzyme is mixed with the protein for a period of time equal to or at least about: 20 minutes, 30 minutes, 40 minutes, 60 minutes, or ranges including and/or spanning the aforementioned values.

In some embodiments, the resulting mixture can be homogenized using a homogenizer. In some embodiments, the homogenization process is performed until a desired viscosity is reached (e.g., equal to or less than about: 10000 cP, 5000 cP, 1000 cP, 500 cP, 100 cP, 5 cP, or ranges including and/or spanning the aforementioned values). In some embodiments, the hydrolyzed protein product is homogenized in a 2-stage homogenizer. In some embodiments, the first stage of the homogenizer is performed using a pressure of equal to or at least about: 2500 psi, 2250 psi, 2000 psi, or ranges including and/or spanning the aforementioned values. In some embodiments, the second stage of the homogenizer is performed using a pressure of equal to or at least about: 1000 psi, 750 psi, 500 psi, or ranges including and/or spanning the aforementioned values. In some embodiments, the homogenization process is performed for a period of time equal to or at least about: 30 minutes, 50 minutes, 60 minutes, 70 minutes, 120 minutes, 180 minutes, or ranges including and/or spanning the aforementioned values.

In some embodiments, a second treatment with alkaline, neutral, acid protease, or combination thereof is performed. In some embodiments, the protease is a endoprotease (e.g., a serine endoprotease). In some embodiments, the protease is an exoprotease. In some embodiments, the protease is selected from the group consisting of DSM Validase FP, DSM BAP, DSM FPC, DSM CPP, DSM AFP, Enzeco Fungal 400, Enzeco BL, Enzeco Fungal Acid, and the like. In some embodiments, the weight ratio % of added protease (based on total dry protein weight) is less than or equal to about: 0.005%, 0.01%, 0.02%, 0.05%, 0.1%, 0.5%, 1.0%, or ranges including and/or spanning the aforementioned values. In some embodiments, enzyme is mixed with the protein for a period of time equal to or at least about: 12 hours, 18 hours, 24 hours, 30 hours, 36 hours, or ranges including and/or spanning the aforementioned values. In some embodiments, the second enzymatic treatment of the protein is performed at a temperature of less than or equal to about: 130° F., 135° F., 140° F., or ranges including and/or spanning the aforementioned values.

In some embodiments, a de-foamer is added to the hydrolyzed protein product solution. In some embodiments, de-foamer is added to provide a solution having a weight ratio % of de-foamer to dry weight solids that is equal to or less than about: 0.1%, 0.05%, 0.01%, 0.005%, 0.0025%, 0.001%, or ranges including and/or spanning the aforementioned values. In some embodiments, the de-foamer is a food grade de-foaming agent (e.g., one or more of Magrabar Organic 3000 de-foamer, Organic 3300, or the like). In some embodiments, the de-foamer is an organically certifiable de-foamer. In some embodiments, a solution of hydrogen peroxide is added to the solution. In some embodiments, hydrogen peroxide is added to provide a solution having a weight ratio % of 50% hydrogen peroxide solution to dry weight solids that is equal to or less than about: 0.5%, 0.1%, 0.05%, 0.01%, or ranges including and/or spanning the aforementioned values. In some embodiments, the de-foamer and/or hydrogen peroxide containing protein solution is allowed to agitate for a period of time equal to or at least about: 10 minutes, 20 minutes, 30 minutes, 60 minutes, or ranges including and/or spanning the aforementioned values.

In some embodiments, the pH of the treated protein is adjusted with an acid. In some embodiments, the pH is adjusted to be equal to or at least about: 7.0, 7.5, 8.0, or ranges including and/or spanning the aforementioned values. In some embodiments, the pH is adjusted by adding one or more of an organic acid or base. In some embodiments, the organic acid is citric acid and the base is NaOH or KOH.

In some embodiments, the modified hydrolyzed protein product can be homogenized using a homogenizer. In some embodiments, the homogenization process is performed until a desired viscosity is reached (e.g., equal to or less than about: 10000 cP, 5000 cP, 1000 cP, 500 cP, 100 cP, 5 cP, or ranges including and/or spanning the aforementioned values). In some embodiments, the homogenizer is operated at a pressure of equal to or at least about: 2500 psi, 2250 psi, 2000 psi, 1000 psi, 750 psi, 500 psi, or ranges including and/or spanning the aforementioned values. In some embodiments, the hydrolyzed protein product is homogenized in a 2-stage homogenizer. In some embodiments, the first stage of the homogenizer is performed using a pressure of equal to or at least about: 2500 psi, 2250 psi, 2000 psi, or ranges including and/or spanning the aforementioned values. In some embodiments, the second stage of the homogenizer is performed using a pressure of equal to or at least about: 1000 psi, 750 psi, 500 psi, or ranges including and/or spanning the aforementioned values. In some embodiments, the homogenization process is performed for a period of time equal to or at least about: 30 minutes, 60 minutes, 120 minutes, 180 minutes, or ranges including and/or spanning the aforementioned values.

In some embodiments, the protein solution is then heated to a temperature of greater than or equal to about: 190° F., 195° F., 200° F., or ranges including and/or spanning the aforementioned values. In some embodiments, once this temperature is reached it is held for a period of at least about: 15 minutes, 10 minutes, 5 minutes, or ranges including and/or spanning the aforementioned values. This heating step can kill microbes present in the product preventing any microbial infection that might have occurred during the processing and transfer of the protein solution. In some embodiments, the rice solution is then spray-dried in a tall form dryer. In some embodiments, the drying process is conducted at a temperature of greater than or at least about: 350° F., 410° F., 450° F., 550° F., or ranges including and/or spanning the aforementioned values.

In some embodiments, the dried powder is sifted and run through a metal detector and then bagged for warehousing. In some embodiments, the dried protein product powder is subjected to one or more of the following: sifting through a 40 mesh sifter, checked for metal shavings through a magnetic metal detector, bagged in 20 kg bags or totes with appropriate product and tracking labels attached, and then sent to warehousing until ready to ship.

A flow diagram outlining an embodiment of the method of preparing the rice protein disclosed in this section is provided in FIG. 5.

In some embodiments, the protein product is advantageously smoother product and suspendable product than available rice protein products. In some embodiments, the protein product remains suspended in water for longer periods than available rice protein products. In some embodiments, upon mixing about 20 g of the protein product in 12 fluid ounces of water, the product remains in suspension without visible and/or measurable sedimentation for a period of equal to or at least about: 15 minutes, 30 minutes, 60 minutes, 120 minutes, or ranges including and/or spanning the aforementioned values. In some embodiments, upon mixing about 20 g of the protein product in 12 fluid ounces of water, the product remains in suspension without visible and/or measurable sedimentation for a period of equal to or at least about: a week, a month, two months, six months, or ranges including and/or spanning the aforementioned values.

Protein Product

In some embodiments, a rice-derived protein product is provided. In some embodiments, the protein product is derived from a brown rice. FIG. 6 provides the amino acid profile of an embodiment of a protein product made using a method as disclosed herein. In some embodiments, the protein product is a rice protein isolate.

In some embodiments, the protein product is a grain or plant-derived protein isolate. In some embodiments, the source of protein within the protein product (e.g., a nutritional supplement) consists only of rice protein and lacks other protein sources. In some embodiments, the source of protein within the protein product consists only of plant protein and lacks other protein sources. As used herein, the term "protein isolate" includes compositions containing protein (including intact proteins, polypeptides, oligopeptides, and/or amino acids) that have been harvested from naturally occurring protein sources. The term protein isolate includes concentrates and hydrolysates of protein from naturally occurring protein sources. The term protein isolate also may include amino acids (whether in monomeric, oligomeric, or polymeric form) that have been concentrated or processed from their native sources via hydrolysis, enzymatic degradation, fermentation, and/or other techniques. In some embodiments, the dry protein by weight in a protein isolate is equal to or at least about: 30%, 40%, 50%, 60%, 70%, 80%, 90%, 100%, or ranges including and/or spanning the aforementioned values. In some embodiments, the protein product comprises only protein (e.g., proteins, polypeptides, oligopeptides, and/or amino acids).

In some embodiments, a gram of the protein product comprises alanine in an amount (in mg) equal to or greater than about: 60, 58, 50, 40, or ranges including and/or spanning the aforementioned values.

In some embodiments, a gram of the protein product comprises arginine in an amount (in mg) equal to or greater than about: 80, 70, 60, 50, 40, 30, 20, 10, or ranges including and/or spanning the aforementioned values.

In some embodiments, a gram of the protein product comprises aspartic acid in an amount (in mg) equal to or less than about: 100, 90, 80, 75, 70, 60, or ranges including and/or spanning the aforementioned values.

In some embodiments, a gram of the protein product comprises cysteine in an amount (in mg) equal to or less than about: 40, 30, 20, 10, or ranges including and/or spanning the aforementioned values.

In some embodiments, a gram of the protein product comprises glutamic acid in an amount (in mg) equal to or less than about: 190, 180, 170, 160, 150, 140, or ranges including and/or spanning the aforementioned values.

In some embodiments, a gram of the protein product comprises glycine in an amount (in mg) equal to or less than about: 60, 50, 45, 40, 30, or ranges including and/or spanning the aforementioned values.

In some embodiments, a gram of the protein product comprises histidine in an amount (in mg) equal to or less than about: 30, 20, 10, 5, or ranges including and/or spanning the aforementioned values.

In some embodiments, a gram of the protein product comprises isoleucine in an amount (in mg) equal to or greater than about: 50, 45, 42, 40, 30, or ranges including and/or spanning the aforementioned values.

In some embodiments, a gram of the protein product comprises leucine in an amount (in mg) equal to or greater than about: 90, 85, 80, 70, 60, or ranges including and/or spanning the aforementioned values.

In some embodiments, a gram of the protein product comprises lysine in an amount (in mg) equal to or greater than about: 40, 35, 30, 20, or ranges including and/or spanning the aforementioned values.

In some embodiments, a gram of the protein product comprises methionine in an amount (in mg) equal to or greater than about: 40, 35, 30, 28, 20, 10, or ranges including and/or spanning the aforementioned values.

In some embodiments, a gram of the protein product comprises phenylalanine in an amount (in mg) equal to or less than about: 80, 70, 60, 55, 50, 40, 30, or ranges including and/or spanning the aforementioned values.

In some embodiments, a gram of the protein product comprises proline in an amount (in mg) equal to or less than about: 60, 55, 50, 45, 40, 30, or ranges including and/or spanning the aforementioned values.

In some embodiments, a gram of the protein product comprises serine in an amount (in mg) equal to or less than about: 60, 55, 50, 45, 40, 30, or ranges including and/or spanning the aforementioned values.

In some embodiments, a gram of the protein product comprises threonine in an amount (in mg) equal to or less than about: 50, 40, 36, 30, 20, or ranges including and/or spanning the aforementioned values.

In some embodiments, a gram of the protein product comprises tryptophan in an amount (in mg) equal to or greater than about: 30, 20, 15, 10, or ranges including and/or spanning the aforementioned values.

In some embodiments, a gram of the protein product comprises tyrosine in an amount (in mg) equal to or greater than about: 60, 50, 40, 30, or ranges including and/or spanning the aforementioned values.

In some embodiments, a gram of the protein product comprises valine in an amount (in mg) equal to or greater than about: 70, 60, 50, 40, or ranges including and/or spanning the aforementioned values.

General Features and Equipment Considerations

In some embodiments, along with the paddy rice material the other major incoming resource is the plant water. In some embodiments, depending on its quality the water desired, water can be softened to less than 1 grain of hardness using a commercial water softener (e.g., with a plurality (2, 3, 4, or more) of resin beds). In some embodiments, the incoming (hard) water is pumped through resin beds until the resin bed is saturated and the softened water no longer meets the desired water softness. In some embodiments, the incoming water is then directed automatically to the next resin bed for softening and the spent resin bed is regenerated by backwashing this resin bed with salt (NaCl) brine an external in ground salt storage facility. In some embodiments, this sequencing of the resin beds is a continuous ongoing process to ensure the plant is provided with proper quality water for all of the plant process needs. In some embodiments the process water is treated with RO membrane technology to get the hardness to less than 1 grain.

Filter Press: In some embodiments, a filter press is used to separate the protein fraction from the maltodextrin fraction. In some embodiments, an automated filter press is used. In some embodiments, the filter press used is manufactured with a rubber bladder design feature that allows separation of protein from maltodextrin with a 70% reduction in required wash water, as compared with other separation technologies including traditional filter press technology (e.g., a. Although the filter press employs a water filled rubber bladder to press out the residual liquids containing maltodextrin in the press. In some embodiments, the use of the rubber bladder to press out residual liquid containing maltodextrin reduces the amount of wash water required as there is a second bladder press step after washing the cake which results in a dramatically reduced wash water usage. This reduction in wash water use to completely wash the maltodextrin out of the protein cake reduces the size of the evaporator by 30-35%, improving the processing. Additionally, in some embodiments, the press is fully automated with belt emptying and washing performed without the touch of an operator. In some embodiments, this reduces the chance of contamination. In some embodiments, the use of the filter press results in significantly lower operating labor to clean the press. In some embodiments, a protein isolate having 82-86% protein in the final protein product is achieved, better than any other product achieved through a standard filter press. In some embodiments, the filter press used is a Filtra Systems (FS) machine. Filter presses have been demonstrated to work efficiently and are often less expensive than several other separation techniques. Maintenance is usually minimal with replacement of the filter cloth as the main maintenance issue and cost.

Decanter Technology: In some embodiments, decanters are used to separate the protein and maltodextrin fraction. In some embodiments, the decanters are operated at commercial scale and provide very good separation and final protein purities in excess of 90%. In some embodiments, decanters are used as an alternative to a filter press (and/or in addition to a filter press or other separation technique disclosed herein). In some embodiments, a decanter provides similar results to a bladder containing filter press. In some embodiments, a series of decanters with tanks and wash systems can be semi-automated to provide the wash cycles needed to remove the maltodextrin from the protein fraction of the enzyme treated rice. In some embodiments, an RO system is used to concentrate the low concentration wash water after the first two rinses. In some embodiments, the RO permeate can be recovered and recycled to reduce the heating energy, water use, and wastewater treatment volumes and associated costs. Unlike filter presses, which may require opening after each press and the cake generally requires some manual scraping to ensure all of the protein is removed (leading potential contamination and protein loss), this separation can be performed with less interaction by workers, etc.

Microfiltration (MF) and/or Ultrafiltration (UF) Membrane Technology: Microfiltration and Ultrafiltration membrane technology can provide very high quality separation of the maltodextrin and protein fractions. In some embodiments, the microfiltration and ultrafiltration membrane system is an easier system to automate and operate in a high yield low bacterial contamination process while providing a very high quality maltodextrin for further processing. In some embodiments, the process technology is combined with one decanter step to increase yield. In some embodiments, as with the decanter, Reverse Osmosis technology can be employed to concentrate the dilute maltodextrin wash water for increasing solids to the evaporator and for recovering rinse water for reuse. Ceramic MF and UF membrane types that can be used include $Al_2O_3$, $TiO_2$, and $ZrO_3$ ceramic membranes with pores sizes between 0.005µ to 2.0µ. Organic membrane types that can be used include spiral, tubular, and plate & frame MF & UF membranes with PVDF, polysulophone, or polyether sulphone membrane chemistries and with membrane pore sizes from 0.005 µm to 1.6 µm. In some embodiments, MF and UF membranes can yield good filtration results. In some embodiments, MF and UF membrane technology is a closed system that is easy to operate and with precise diafiltration rinse water control and will provide hygienic environment for the various products produced. In some embodiments, the separation is can be much finer and more precise resulting in higher protein yields from the separation process and the maltodextrin MF and UF permeate solution will have a very high clarity which will be beneficial from a purity metric and for suitability on broader food applications especially clear beverages. Maintenance on this equipment is generally low simply requiring pump seals to be replaced periodically and valve seats to be replaced when they wear. Unlike filter presses, which may require opening after each press and the cake generally requires some manual scraping to ensure all of the protein is removed (leading potential contamination and protein loss), this separation can be automated and performed without interaction by workers, etc.

Protein Spray Drier: In some embodiments, the protein spray drier is a tall form single stage tower spray drier or a box dryer, both with high pressure nozzle atomization. In some embodiments, protein is removed from the main drying chamber through a bustle to a primary cyclone, then to a baghouse to remove final protein powder. In some embodiments, the water evaporation design for the drier is at least about 10,000 pounds of water removal per hour producing 1,891 pounds of 4-5% moisture protein powder per hour. In some embodiments, the water is evaporated by air that has been heated using a direct fired natural gas low NOX burner. In some embodiments, the powder is removed from the drier bottom, cyclone, and baghouse and pneumatically conveyed to one of two protein product storage bins in the drier tower for storage before packaging. In some embodiments, a CIP system for wet cleaning of the dryer is provided. In some embodiments, it is not necessary to clean this spray drier.

Liquid Rice Syrup Evaporator: In some embodiments, the evaporator is a multi-effect mechanical vapor recompression evaporator (depending on final capital/operating costs analysis). In some embodiments, the liquid maltodextrin discharged from the protein separation equipment noted above is comingled with syrup wash water discharged from the separation wash solutions and then concentrated with Reverse Osmosis technology to about 20% total solids. In some embodiments, the RO concentrated carbohydrate mixture is fed to one of the stages of the evaporator to increase solids from about 20% to 35% or 50% depending on the final solids requirements of the deionization system design criteria. In some embodiments, the maltodextrin solution is enzyme treated to produce a high dextrose equivalent rice syrup product. In some embodiments, if this product is derived from the decanter or filter press technologies the syrup is clarified (through diatomatious earth or other suitable depth filtration step). If this product is derived from MF or UF membrane technology the filtrate will be crystal clear and will not require any further filtration for clarification. In some embodiments, a maltodextrin fraction from a MF or UF separation process can be sent directly to a deionization system. In some embodiments, the deionized rice syrup product is then moved back to last effects in the evaporator to be concentrated to a final Brix of about 80° (or other brix values as disclosed elsewhere herein).

Wet Milling/Colloid Mills: In some embodiments, a wet milling process is used whereby the particle size of the raw material white rice and/or brokens is reduced. In some embodiments, the wet milling is done by utilizing a coarse colloid mill followed by a fine colloid mill which have a fixed stator and variable spaced rotor. In some embodiments, the wet mill has the ability to vary the grind size and/or throughput by adjusting the clearance between the stator and rotor.

Homogenization and Pasteurization: In some embodiments, the rice protein streams are processed through a homogenizer to smooth out any agglomerated particles and/or lumps in these products just prior to maltodextrin separation from the protein. In some embodiments, the homogenizers are outfitted with about 5000 psi maximum pressure heads to and each outfitted with two stage homogenization valves which operate at about 2500/500 psi (or other pressures as disclosed elsewhere herein) respectively for the two stage operation which also serve as a timing pump to feed the pasteurization system for each product. In some embodiments, the rice maltodextrin and protein streams are heated to pasteurization temperatures with a shell and tube heat exchanger with steam as the heading medium on the shell side with condensate return to the boilers. In some embodiments, the products are pumped using the homogenizer through the shell and tube pasteurizers with product temperature controlled by instrumentation to throttle the steam supply to accomplish a consistent pasteurization temperature. In some embodiments, the product is held for a specific time by installation of a hold tube with a back pressure valve to maintain flow and pasteurization temperature. In some embodiments, each pasteurizer has an automatic recycle and divert valve back to the pasteurizer feed tank in the event that the pasteurization temperature does not meet a minimum set point. In some embodiments, a part of the protein pasteurization is a baffled surge tank just before the protein spray drier as a part of the holding time to denature enzymes.

Syrup De-ionization System: In some embodiments, the rice syrup is deionized with a resin based deionization system with both anionic and cationic deionization beds. In some embodiments the raw syrup will be passed through an activated charcoal column and/or a UF or NF membrane system to remove color and residual protein in the solution that could reduce the deionization efficiency and cleaning. In some embodiments, the system has three identical sections whereby two sections will operate simultaneously with the first section removing 90% of the ions and the second section polishing the last 10% of the ions from the stream. In some embodiments, when the first section resin beds are "saturated" they are taken out of operation, rinsed to remove the remaining "sweet water" and then the resins are regenerated. In some embodiments, the second section becomes the primary ion removal section and the third section is the polishing section. In some embodiments, the second section becomes "saturated" it is taken out of line like the first section and regenerated. In some embodiments, the third section will become the primary ion removal section and the first section becomes the polishing section. In some embodiments, the process can be cycled like this 24/7 while production is underway. In some embodiments, the equipment to be provided is by Pro Sep or others.

Husk and Bran Removal: In some embodiments, the husk and bran are removed from the paddy rice with a series of equipment and process steps. In some embodiments, one or more of the following pieces of equipment are used for husk and/or bran removal from grain rice or rice brokens. In some embodiments, each of the following pieces of equipment are used for husk and/or bran removal from grain rice or rice brokens. In some embodiments, the equipment can be supplied by Zaccaria or others.

Husk Removal: In some embodiments, paddy rice impurities and stones are removed and husks are removed using one or more of: a screen cleaner; destoner; a continuous weigher; a husk remover; a dust remover/collector; a husk transport to storage pneumatic transport; blowers; and conduit.

Bran Removal: In some embodiments, bran removed from the rice is heat treated to deactivate the lipase enzyme, and the oil and bran separated.

Oil Press: In some embodiments, oil is removed from the bran using an oil press. In some embodiments, oil is removed using one or more of a screw press, a coarse filter, or both. Oil Packaging: in some embodiments, the oil from the bran is collected (and packaged in drums or totes).

In some embodiments, the transport of the dry raw material (e.g., rice, dehusked rice, etc.) throughout plant is accomplished with pneumatic conveyors. In some embodiments, the a particle size of 95% passing through a 60 mesh screen is an used for dry milling preparation. Due to hard nature of the dry rice it is very abrasive causes significant wear on all milling equipment. In some embodiments, as disclosed elsewhere herein, an alternative to dry milling of the white rice/brokens is to process the white rice/brokens slurry using wet milling technologies. In some embodiments, the steeping the raw rice in water for about 30 minutes at about 170° F. to 195° F. (e.g., 185° F.). In some embodiments, the steeped white rice/brokens can then be wet milled. In some embodiments, the wet milling is easier to accomplish with less wear on the surfaces of the equipment performing the size reduction. Various trial runs indicate that a fine milling is better than a milling that is too coarse.

Evaporator Condensate Water: In some embodiments, the evaporator condensate water (ECW) from the liquid rice syrup concentrated in the evaporator is used as process makeup water. In some embodiments, the ECW is used as makeup water for the boiler and non-final rinse CIP make-up water. In some embodiments, the method comprises collecting the ECW and polishing it with an RO system to remove any solids and sending high purity water back to the plant to reuse. This not only reduces effluent volumes but also reduces water demand and cost of softening while recovering the heat energy held in the ECW.

Rinse Water from Protein Separations: The decanter, microfiltration, ultrafiltration, vibrating screen filter, incline screen filter, and to a lesser degree the FS Filter and filter press alternatives all generate dilute water that needs to have the sugars recovered and concentrated for syrup production. In some embodiments, RO technology can be applied to cost effectively remove and purify the water from these processes. In some embodiments, the permeate from the primary RO system processing this rinse water can be blended with the ECW above and further polished through a second RO system for reuse. The resulting water is of much higher purity than tap water and when heat treated will be essentially void of microbial contaminates. In some embodiments, the solids from the primary RO retentate will contain the maltodextrin fractions and so maximal yield will need to be obtained from this part of the process. In some embodiments, the secondary polishing RO generates high purity water for reuse. In some embodiments, the retained valuable solids can be recycled back up at the front in the high temperature steeping process to increase yields and recover heat while reducing make-up and softened water demand.

Rinse Water from Clean in Process (CIP): In some embodiments, the rinse water from the CIP operations can be collected and used as make-up water in the CIP process recovering water and its thermal content. In some embodiments, it is desired to have only the actual cleaning solutions used to clean the tanks disposed of to the waste water treatment plant along with any floor and housekeeping wash water.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

CONCLUSION

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Some embodiments provide method to isolate and purify (and/or further process) maltodextrin fractions and protein fractions from rice during the same process. In other words, in some embodiments, proteins and maltodextrin are advantageously isolated from rice in a single process. Conventionally, when maltodextrin is isolated from rice, the protein fraction is discarded as a waste product. Similarly, starch fractions are treated as waste products in the isolation of proteins from rice. Advantageously, using the methods disclosed herein, both high quality rice syrups and high quality protein products can be obtained from the same rice source (or other grain).

With respect to the use of substantially any plural and/or singular terms herein, those having skill in the art can translate from the plural to the singular and/or from the singular to the plural as is appropriate to the context and/or application.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. For example, "an" agent can include one, two or several ingredients (and not necessarily a single ingredient). In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth. The phrases "and ranges in between" can include ranges that fall in between the numerical values listed. For example, "1, 2, 3, 10, and ranges in between" can include 1-10, 1-3, 2-10, etc.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

For the methods disclosed herein, the functions performed in the processes and methods may be implemented in differing order. The disclosure of methods or uses may also include instructing the method or use (for example, in instructions for use).

What is claimed is:

1. A method of manufacturing rice syrup and a hydrolyzed protein from rice, the method comprising:
    treating the rice with water to prepare a hydrated rice;
    milling the hydrated rice to form a milled rice slurry;
    agitating the slurry with an α-amylase enzyme until a mixture of dissolved maltodextrin and suspended protein is formed;
    homogenizing the maltodextrin and suspended protein to form a homogenous mixture;
    separating the protein and maltodextrin into an isolated protein fraction and an isolated maltodextrin fraction;
    treating the isolated maltodextrin fraction with glucoamylase to provide a rice syrup wherein the rice syrup has a dextrose equivalent ranging from 43 to 98; and
    treating the isolated protein fraction with a hydrolyzing agent to provide a hydrolyzed protein.

2. The method of claim 1, wherein the hydrolyzing agent is a protease enzyme.

3. The method of claim 1, further comprising homogenizing the hydrolyzed protein using a two-stage homogenizer.

4. The method of claim 1, wherein the hydrolyzed protein is dried by a process selected from the group consisting of spraying into a dryer, evaporating at reduced temperature and/or under reduced pressure, by heating, and combinations thereof.

5. The method of claim 4, wherein the hydrolyzed protein is dried to a powder; wherein upon mixing about 20 g of the protein powder in 12 fluid ounces of water, the protein product remains in suspension without visible and/or measurable sedimentation for a period of at least about a week.

6. The method of claim 1, further comprising passing the rice syrup through an activated charcoal column, and/or a UF membrane, and/or a NF membrane or any combination thereof.

7. The method of claim 1, further comprising passing the rice syrup through a de-ionizing column.

8. The method of claim 1, wherein the protein and maltodextrin are separated from one another using one or more of decanters, microfiltration membrane systems, ultrafiltration membrane systems, vibrating screen filter, incline screen filter, filter presses, or combinations thereof.

9. The method of claim 1, wherein the pH of the isolated protein fraction is adjusted with a base prior to treatment with a hydrolyzing agent.

* * * * *